(12) United States Patent
Kaufman et al.

(10) Patent No.: US 7,553,484 B2
(45) Date of Patent: Jun. 30, 2009

(54) MODULATING NEURONAL OUTGROWTH VIA THE MAJOR HISTOCOMPATIBILITY COMPLEX CLASS I (MHC I) MOLECULE

(75) Inventors: Daniel L. Kaufman, Los Angeles, CA (US); Lorraine Hanssen, Los Angeles, CA (US); Dan Zekzer, Encinitas, CA (US)

(73) Assignee: The Regents of the University of California

( * ) Notice: Subject to any disclaimer, the term of this patent is extended or adjusted under 35 U.S.C. 154(b) by 275 days.

(21) Appl. No.: 10/161,647

(22) Filed: Jun. 5, 2002

(65) Prior Publication Data

US 2003/0049254 A1 Mar. 13, 2003

Related U.S. Application Data

(60) Provisional application No. 60/295,596, filed on Jun. 5, 2001.

(51) Int. Cl.
*A61K 39/395* (2006.01)
*A61K 39/00* (2006.01)

(52) U.S. Cl. ............... 424/130.1; 424/141.1; 424/184.1
(58) Field of Classification Search ................ None
See application file for complete search history.

(56) References Cited

U.S. PATENT DOCUMENTS

| | | | |
|---|---|---|---|
| 3,654,090 A | 4/1972 | Schuurs et al. | |
| 3,850,752 A | 11/1974 | Hermanus et al. | |
| 4,016,043 A | 4/1977 | Schuurs et al. | |
| 4,341,761 A | 7/1982 | Ganfield et al. | |
| RE31,006 E | 8/1982 | Schuurs et al. | |
| 4,342,566 A | 8/1982 | Theofilopolous et al. | |
| 4,399,121 A | 8/1983 | Albarella et al. | |
| 4,427,783 A | 1/1984 | Newman et al. | |
| 4,444,887 A | 4/1984 | Hoffmann | |
| 4,451,570 A | 5/1984 | Royston et al. | |
| 4,466,917 A | 8/1984 | Nussenzweig et al. | |
| 4,472,500 A | 9/1984 | Milstein et al. | |
| 4,491,632 A | 1/1985 | Wands et al. | |
| 4,493,795 A | 1/1985 | Nestor et al. | |
| 4,493,890 A | 1/1985 | Morris | |
| 4,816,567 A | 3/1989 | Cabilly et al. | |

OTHER PUBLICATIONS

Lyons et al. (1994). PNAS. 91, 3191-3195.*
Campbell et al. (1999). Neuroreport. Abstract only.*
Yagita et al (1996). Life Sciences. 59, 1643-1650.*
Gold et al. (1995). J. Neurosci. 15, 7509-7516.*
Lee et al. (2005). Blood. 105, 3951-3955.*
Linda et al (1998). Experimental Neurology. 150, 282-295.*
Korr et al., 150 Journal Complete Neurology 169 (1971).
Wolsqijk and Noble, 105 Development 387 (1989).
Recio-Pinto et al., 6 Journal of Neuroscience 1211-19 (1986).
Near et al., 89(11) Proceedings of the National Academy of Science 11716-11720 (1992).
Edbladh et al, 641 Brain Research 76-82 (1994).
Gospodarowicz et al., 19 Cell Differentiation 1-17 (1986).
M.A. Walter et al., 12 Lymphokine Cytokine Research 135-141 (1993).
B.S. McEwen et al., 87 Developmental Brain Research 91-95 (1995).
C. Dominique Toran-Allerand et al., 56 Journal of Steroid Biochemistry and Molecular Biology 169-78 (1996).
Lyons et al., 91 Proceedings of the National Academy of Science 3191-5 (1994).
Sharkey and S.P. Butcher, 371 Nature 336-9 (1994).
Gold et al., 15 Journal of Neuroscience 7509-16 (1995).
I. Aubert et al., 5 Current Opinion in Neurobiology 625-635 (1995).
H. Lodish et al., Molecular Cell Biology 3d. Ed. (1995).
H. Song & M. Poo, 9 Current Opinion in Neurobiology 355-363 (1999).
R.A. Segal & M.E. Greenberg, 19 Annual Review of Neuroscience 463-489 (1996).
Q. Wang & J.Q. Zheng, 18 Journal of Neuroscience 4973-4984 (1998).
M. Hamelin et al., 364 Nature 327-330 (1993).
K. Keino-Masu et al., 87 Cell 175-185 (1996).
G.L. Ming et al., 19 Neuron 1225-1235 (1997).
A. Chedotal et al., 125 Development 4313-4323 (1998).
Z. He & M. Tessier-Lavigne, 90 Cell 739-751 (1997).
M.L. Winberg, 95 Cell 903-916 (1998).
H. Song et al., 281 Science 1515-1518 (1998).
P. Caroni & M.E. Schwab, 1 Neuron 85-96 (1988).
P.W. Johnson et al, 3 Neuron 377-385 (1989).
G. Mukhopadhyay et al., 13 Neuron 757-767 (1994).

(Continued)

*Primary Examiner*—Dong Jiang
*Assistant Examiner*—Sandra Wegert
(74) *Attorney, Agent, or Firm*—Bingham McCutchen LLP

(57) ABSTRACT

The invention relates to methods and compositions for treating neural damage caused by injury or disease, by enhancing neural outgrowth and/or repair responses in the nervous system. Preferably, the methods and compositions utilize agents which interfere with the ability of the major histocompatibility complex (MHC) Class I molecule (MHC I) to inhibit neurite outgrowth. Such agents include antibodies directed to MHC I, MHC I fragments and/or analogs, and agents which interfere with MHC I interaction with its neuronal receptor and the receptor's signaling pathway.

7 Claims, 5 Drawing Sheets

OTHER PUBLICATIONS

M.S. Chen et al., 403 (6768) Nature 434-439 (2000).
Zijlstra et al., 344 Nature 742-6 (1990).
Williams et al., 142 Journal of Immunology 2796-806 (1989).
Heemels and Ploegh, 64 Annual Review of Biochemistry 463-91 (1995).
Viret and Janeway, Jr., 1 Review of Immunogenetics 91-104 (1999).
Natarajan et al., 1 Review of Immunogenetics 32-46 (1999).
Jackson and Peterson, 9 Annual Review of Cell Biology 207-35 (1993).
S. Agrawal and M. Kishore, 9 Journal of Hematotherapy & Stem Cell Research 795-812 (2000).
van den Elsen PJ et al, 19 Immunology Today 308-312 (1998).
A. R. Vora et al., 76 British Journal of Cancer 836-844 (1997).
P.A. Burke and K. Ozato, 4 The Year in Immunology 23-40 (1989).
B. David-Watine, 11 Immunology Today 286-292 (1990).
O. Yano et al., 6 Journal of EMBO 3317-3324 (1987).
A.S. Baldwin and P.A. Sharp, 85 Proceedings of the National Academy of Sciences U.S.A. 723-727 (1988).
K. Kawakami et al., 85 Proceedings of the National Academy of Sciences USA 4700-4704 (1988).
T. Nakamura et al., 10 Molecular Cell Biology 3700-3708 (1990).
Israel, A., et al., 8 Journal EMBO 3793-3800 (1989).
S. J. Gobin et al., 1 Seminars in Cancer Biology 55-59 (1999).
Berg and Kang, 13 Current Opinions in Immunology 232-41 (2001).
Nemazee, 18 Annual Review of Immunology 19-51 (2000).
Matzinger, 12 Annual Review of Immunology 991-1045 (1994).
van Leeuwen and Samelson, 11 Curret Opinions in Immunology 242-8 (1999).
Bromley et al., 19 Annual Review of Immunology 375-96 (2001).
E. Joly et al, 253 Science 1283-5 (1991).
L.A. Lampson 32 Microscopy Research and Technique 267-85 (1995).
H. Neumann et al., 269 Science 549-52 (1995).
H. Neumann et al., 185 Journal of Experimental Medicine 305-16 (1997).
O. Lidman et al., 11 European Journal of Neuroscience 4468-72 (1999).
R.A. Corriveau et al., 21 Neuron 505-20 (1998).
G.S. Huh et al., 290 Science 2155-9 (2000).
Cotman et al., 70(12) Proceedings of the National Academy of Sciences, USA 3473-3477 (1973).
Lynch et al., 180(93) Science 1364-1366 (1973).
Steward et al., 18(4) Experimental Brain Research 396-414 (1973).
Hedreen et al., 33(2) Journal of Histochemistry and Cytochemistry 134-140 (1985).
Scheff and Cotman, 21(2) Behavioral Biology 286-293 (1977).
Sambrook et al., "Molecular Cloning: A Laboratory Manual" (3$^{rd}$ edition, 2001).
"Current Protocols in Molecular Biology" vols. I-III, (Ausubel, R.M., ed. 1999 and updated biomonthy).
"Cell Biology: A Laboratory Handbook" vols. I-III (J.E. Celis, ed. 1994).
"Current Protocols in Immunology" vols. I-IV (Coligan, J. E., ed. 1999 and updated bimonthly).
"Oligonucleotide Synthesis," (M.J. Gait, ed. 1984).
"Nucleic Acid Hybridization," (B.D. Hames & S.J. Higgins, eds. 1985).
"Transcription And Translation," (B.D. Hames & S.J. Higgins, eds. 1984).
"Culture of Animal Cells, 4$^{th}$ Edition," (R.I. Freshney, ed. 2000).
"Immobilized Cells And Enzymes" (IRL Press, (1986).
B. Perbal, "A Practical Guide To Molecular Cloning" (1988).
Using Antibodies: A Laboratory Manual: Portable Protocol No. I, Harlow, Ed and Lane, David (Cold Spring Harbor Press, 1998).
Using Antibodies: A Laboratory Manual, Harlow, Ed and Lane, David (Cold Spring Harbor Press, 1999).
"G Protein-Coupled Receptors" (T. Haga et al., eds. 1999).
Kohler et al., 256 Nature 495-7 (1975).
Clackson et al., 352 Nature 624-8 (1991).
Marks et al., 222 J. Mol. Biol 581-97 (1991).
Maniatis et al., *supra*; DNA Cloning, vol. I & II, *supra*; Nucleic Acid Hybridization, *supra*.
Jun et al., 164(2) Journal of Immunology 805-11 (2000).
Ma and Niederkorn, 86(2) Immunology 263-9 (1995).
Mosmann, 56 Advances in Immunology 1-26 (1994).
S.I. Tanaguchi et al., 12 Molecular Endocrinology 19-33 (1998).
Ploegh, 280 Science 248-253 (1998).
York and Rock, 14 Annual Review of Immunology 369-396 (1996).
Charlton and Zmijewski, 170 Science 636-7 (1970).
Allison et al, 118 Journal of Immunology 1004-9 (1977).
F. Puppo et al., 53 Tissue Antigens 253-62 (1999).
M.S. Krangel 163 Journal of Experimental Medicine 1173-90 (1986).
Y. Zhai and S. Knechtle, 59 Human Immunology 404-14 (1998).
Pickl et al., 151 Journal of Immunology 2613-22 (1993).
M. Schreier et al., Hybridoma Techniques (1980).
Hammerling et al., "Monoclonal Antibodies And T-cell Hybridomas" (1981).
Harlow and Lane, A Laboratory Maunal, Cold Spring Harbor Laboratory, New York (1988).
Kennett et al., "Monoclonal Antibodies" (1980).
Dulbecco et al., 8 Virology 396 (1995).
Niman et al., 80 Proceedings of the National Academy of Sciences, U.S.A. 4949-4953 (1983).
Edge, 292 Nature 756-762 (1981).
Nambair et al., 223 Science 1299-1301 (1984).
Jay et al., 259 Journal of Biology and Chemistry 6311-6317 (1984).
Noren et al., 244 Science 182-188 (Apr. 1989).
Remington, Pharmaceutical Science, 17$^{TH}$ Ed (1985).
Rall et al, (1995) 182(5) Journal of Experimental Medicine 1201-1212 (1995).
D. Gussow and H. Ploegh, 8 Immunology Today 220-2 (1987).
R. Buelow et al., 59(5) Transplantation 649-654 (1995).
Linda et al., 150(2) Experimental Neurology 282-295 (1998).
Linda et al., 101(1) Journal of Neuroimmunology 76-86 (1999).
Wong et al., 310(5979) Nature 688-691 (1984).
Drew et al., 150(8, Part 1) Journal of Immunology 3300 (1983).
O'Malley and MacLeish, 43(1-2) Journal of Neuroimmunology 45-57 (1993).
Feurestein et al., 5(3-4) Neuroimmunomodulation 143-159 (1998).
Lynch et al., 42(2) Brain Research 311-318 (1972).
Steward, 194(4263) Science 426-428 (1976).
Scheff, et al. 199(1) Brain Research 21-38 (1980).
Stanfield and Cowan, 232(1) Brain Research 162-170 (1982).
Frotscher et al., 20(5) Trends in Neuroscience 218-223 (1997).
Ramirez, 73 Advanced Neurology 61-82 (1997).
Douglas and Raphelson 62(2) Journal of Comparative Physiology and Psychology 320-322 (1966).
Lanier, 16 Annual Review of Immunology 359-393 (1998).

\* cited by examiner

MODULATING NEURONAL OUTGROWTH VIA THE MAJOR HISTOCOMPATIBILITY COMPLEX CLASS I (MHC I) MOLECULE

CROSS-REFERENCE TO RELATED APPLICATIONS

This application claims priority from U.S. Provisional Application Serial No. 60/295,596, filed Jun. 5, 2001, which is incorporated by reference herein in its entirety for all purposes.

BACKGROUND OF THE INVENTION

1. Field of the Invention

The present invention relates to methods and compositions for treating neural damage caused by injury or disease, by enhancing neural outgrowth and/or repair responses in the nervous system. Preferably, the methods and compositions utilize agents which interfere with the ability of the major histocompatibility complex (MHC) Class I molecule (MHC I) to inhibit neurite outgrowth.

2. Description of the Related Art

Brain Disorders

An estimated 5.3 million Americans, over 2% of the United States' population, currently live with disabilities resulting from brain injury. Vehicle crashes are the leading cause of brain injury and account for 50% of all traumatic brain injuries. Falls are the second leading cause of brain injury, and are the leading cause of brain injury in the elderly. Brain injuries can affect a person cognitively, physically, and emotionally. These injuries are estimated to cost the United States over $48 billion annually.

Approximately 4 million Americans currently have Alzheimer's disease. Alzheimer's disease is a progressive, degenerative disease of the brain. Alzheimer's disease gradually destroys a person's ability to reason, remember, imagine, and learn. Alzheimer's disease victims often suffer from depression, anxiety, and paranoia. Alzheimer's disease is estimated to cost the United States over $100 billion annually.

Unlike the brain injuries discussed at the outset, Alzheimer's disease is not the result of physical trauma to the brain. Instead, Alzheimer's disease is the result of abnormal clumps, termed senile plaques, and irregular knots, known as neurofibrillary tangles, of brain cells. Currently, there is no effective treatment for Alzheimer's disease.

Parkinson's disease is yet another progressive brain disorder that attacks the central nervous system ("CNS"). Over 1 million Americans suffer from Parkinson's disease. Victims of Parkinson's disease experience a decrease in spontaneous movement, gait difficulty, postural instability, rigidity and tremors.

Like Alzheimer's disease, Parkinson's disease is not the result of brain trauma. It is now believed that Parkinson's disease is caused by degeneration of the neurons in the substantia nigra of the brain, which results in decreased dopamine availability. Current treatment of Parkinson's disease consists of administration of the drug L-DOPA. Once in the brain, L-DOPA is converted to dopamine, the same substance found at decreased levels in Parkinson's disease victims. This course of treatment, however, does not prevent the progressive changes of the brain typical of Parkinson's disease victims.

Common among these brain disorders is the effect they have on the mammalian CNS at the anatomical level. It is known that loss of dopaminergic neurons in the substantia nigra is the etiological cause for Parkinson's disease. The neurodegeneration found in Alzheimer's victims may be due to brain inflammation and deposition of beta-amyloid protein and other such agents which inhibit survival of neurons and mitigate the growth of neurites used for communication between neurons. Brain ischemia and spinal cord injuries also result in neuronal cell death.

The mature mammalian CNS is composed of neurons and glial cells, including astrocytes and oligodendrocytes. The mammalian CNS begins to develop in the early stage of fetal development and continues until the post-natal period. The first stage of neural development is cell birth. Cell birth is the precise temporal and spatial sequence in which stem cells and stem cell progeny proliferate. These proliferating cells give rise to neuroblasts, glioblasts, and new stem cells.

The next stage of neural development is a period of cell type differentiation and migration. At this stage, undifferentiated progenitor cells differentiate into neuroblasts and glioblasts, giving rise to neurons and glial cells that migrate to their final positions. Cells derived from the neural tube give rise to neurons and glia of the CNS, whereas cells derived from the neural crest give rise to cells of the peripheral nervous system ("PNS"). Factors that are present during development, such as nerve growth factor ("NGF"), promote the growth of neural cells. NGF is secreted by cells of the neural crest and stimulates the sprouting and growth of neuronal axons.

The third stage of neural development occurs when cells acquire specific phenotypic qualities. One such phenotypic quality is the expression of particular neurotransmitters, for example. At this time, neurons also extend processes which synapse on their targets. These neurons are primarily generated during the fetal period. Oligodendrocytes and astrocytes are primarily generated during the early post-natal period. Accordingly, by the late post-natal period, the mammalian CNS has a full complement of nerve cells.

Then, in the fourth and final stage of neuronal development, selective cell death occurs. During selective cell death, specific cells, fibers, and synaptic connections degenerate or die, causing the complex circuitry of the CNS to be modified. This modification continues throughout the life of the mammal.

Unlike many other cells found in different mammalian tissues, adult mammalian CNS cells have little or no ability to regenerate. This is because differentiated cells of the adult mammalian CNS have little or no ability to enter the mitotic cycle. Although there is a limited and slow turnover of astrocytes (Korr et al., 150 *J. Complete Neurology* 169 (1971)), and although progenitors for oligodendrocytes are present (Wolsqijk and Noble, 105 *Development* 386 (1989)), the generation of new neurons is very limited. However, this very limited ability is a distinct disadvantage with respect to the need to replace lost or damaged synaptic connections.

Current Therapies and Areas of Research for Modulating Neurite Outgrowth

Presently, there is no satisfactory treatment for patients suffering the effects of loss of or of damage to neural tissue. Conventional treatment has been primarily via administration of pharmaceutical compounds. Unfortunately, this type of treatment carries with it many complications, including the limited ability to transport drugs across the blood-brain barrier, and the drug tolerance that is acquired by patients to whom these compounds are given over a long period of time.

To avoid these complications, innovative treatments attempt to promote neuronal sprouting or regeneration of nerves. Innovative treatments comprise the use of growth factors, small molecule therapy, tacrolimus, and manipulation of molecular guidance cues, summarized briefly below. Common among these treatments is the reliance on cellular signaling, which is also summarized briefly below.

1. Growth Factors

Stimulation of neurite outgrowth protects neurons from degeneration, and accelerates the regeneration of nerve cells in individuals suffering from neurological diseases. Neurite outgrowth is also critical to the survival of neurons and is stimulated in vitro by NGFs. For example, Glial Cell Line-Derived Neurotrophic Factor ("GDNF") demonstrates neurotrophic activity both in vitro and in vivo. GDNF is currently being investigated for treatment of Parkinson's disease. Insulin and insulin-like growth factors have been shown to stimulate growth of neurites in rat pheochromocytoma PC12 cells and in cultured sympathetic and sensory neurons. Recio-Pinto et al., 6 *Journal of Neuroscience* 1211-19 (1986). Insulin and insulin-like growth factors also stimulate regeneration of injured motor nerves in vitro and in vivo. Near et al., 89(11) *Proceedings of the National Academy of Science*, 716-720 (1992) and Edbladh et al., 641 *Brain Research* 76-82 (1994). Similarly, fibroblast growth factor ("FGF") stimulates neural proliferation and growth. Gospodarowicz et al., 19 *Cell Differentiation* 1 (1986); M. A. Walter et al., 12 *Lymphokine Cytokine Research* 135 (1993).

However, the use of NGFs for treating neurological diseases presents several distinct disadvantages. NGFs possess poor drug delivery properties. For example, NGFs do not readily cross the blood-brain barrier. Moreover, NGFs are unstable in plasma. Thus, the NGF approach to promoting neurite outgrowth is afflicted with the same complications as conventional CNS disorder therapies.

2. Small Molecule Therapy

Recently, relatively small molecules have been shown to stimulate neurite outgrowth in vivo. One such small molecule, estrogen, has been shown to promote the growth of axons and dendrites, which are neurites sent out by nerve cells to communicate with each other in a developing or injured adult mammalian brain. B. S. McEwen et al., 87 *Developmental Brain Research* 91-95 (1995), and C. Dominique Toran-Allerand et al., 56 *Journal of Steroid Biochemistry and Molecular Biology* 169-78 (1996). Studies have shown that the progress of Alzheimer's disease is slowed in female victims who receive estrogen therapy. It is hypothesized that estrogen complements NGF and other neurotrophins, thereby helping neurons differentiate and survive. However, extensive testing in this area is still needed.

3. Tacrolimus

Other studies have shown that tacrolimus, an immunosuppresive drug, acts synergistically with NGF in stimulating neurite outgrowth in PC12 cells as well as sensory ganglia. Lyons et al., 91 *Proceedings of the National Academy of Science* 3191-5 (1994). Tacrolimus has also been shown to be neuroprotective in focal cerebral ischemia (J. Sharkey and S. P. Butcher, 371 *Nature* 336-9 (1994)), and to increase the rate of axonal regeneration in injured sciatic nerve. Gold et al., 15 *Journal of Neuroscience* 7509-16 (1995). Yet again, extensive study is still needed in this field.

4. Molecular Guidance Cues That Guide Axonal Growth

Recent studies have identified several molecules which are thought to modulate directed growth and target recognition of axons. These molecules either inhibit or promote axonal growth and are believed to be important in the guidance and growth of axons to their appropriate targets after lesions in the adult CNS. Appropriate axonal growth cone guidance is controlled by diffusible or membrane-bound molecules that may act through chemoattraction or chemorepulsion to influence the direction of growth cone extension and target recognition. I. Aubert et al., 5 *Current Opinion in Neurobiology* 625-635 (1995). Many of these molecules are bifunctional, meaning that they induce either attractive or repulsive responses depending on various cellular conditions.

To date, research has shown that several of these guidance molecules share similar mechanisms of action. Though the initial signals for each guidance molecule are different, the downstream mechanisms for many of them involve pathways that modulate cyclic nucleotide levels. H. Lodish et al., *MOLECULAR CELL BIOLOGY*, 3d. Ed. (1995); H. Song & M. Poo, 9 *Current Opinion in Neurobiology* 355-363 (1999). Future research will likely uncover additional molecules that mediate axon growth, and more importantly, the mechanisms of action of all of the molecular guidance cues. Understanding guidance molecules as well as signaling pathways underlying axon growth is essential to developing strategies that block or reverse inhibitory molecules, thereby promoting axon regeneration after injury.

a. Neurotrophins

The earliest known factors involved in axonal growth were the neurotrophins. Neurotrophins include nerve growth factor ("NGF"), brain-derived neurotrophic factor ("BDNF"), and neurotrophin-3 ("NT-3"). Neurotrophins bind ligand specific receptor tyrosine kinases which activate multiple intracellular signaling pathways, including cyclic nucleotide dependent pathways. R. A. Segal & M. E. Greenberg, 19 *Annual Review of Neuroscience* 463-489 (1996); H. Song & M. Poo, 9 *Current Opinion in Neurobiology* 355-363 (1999). BDNF has been shown to act as either an attractant or a repellent depending on the levels of adenosine 3',5'-monophosphate (cAMP) signaling. Q. Wang & J. Q. Zheng, 18 *Journal of Neuroscience* 4973-4984 (1998).

b. Netrins

Netrins are a family of secreted proteins that bind to two receptor types, DCC and UNC, and can induce attractive or repulsive responses—depending on the type of receptor expressed. M. Hamelin et al., 364 *Nature* 327-330 (1993); K. Keino-Masu et al., 87 *Cell* 175-185 (1996). Studies have shown that the normal chemoattractive response to netrin (binding to DCC receptor) can be converted to a chemorepulsive response in the presence of a competitive analog of cAMP or an inhibitor of protein kinase A. This phenomenon suggests that the action of netrin is dependent upon the intracellular levels of cAMP. G. L. Ming et al., 19 *Neuron* 1225-1235 (1997).

c. Semaphorins

Semaphorins are a family of secreted and membrane-bound proteins that act as repulsive guidance cues to axonal growth cones. A. Chedotal et al., 125 *Development* 4313-4323 (1998). There are two receptor types, neurophilins and plexins, that bind semaphorins. Z. He & M. Tessier-Lavigne, 90 *Cell* 738-751 (1997); M. L. Winberg, 95 *Cell* 903-916 (1998). Research has shown that the pharmacological activation of the guanosine 3',5'-monophosphate (cGMP) signaling pathway can convert semaphorin-induced repulsion to attraction. H. Song et al., 281 *Science* 151-154 (1998).

d. Myelin-Associated Growth Inhibitors

Myelin-associated growth inhibitors are another group of guidance molecules. Many myelin-associated growth inhibitors are recognized by the monoclonal antibody IN-1, which is an antibody that can neutralize the inhibitory effects of myelin proteins. P. Caroni & M. E. Schwab, 1 *Neuron* 85-96 (1988). Myelin-associated glycoprotein ("MAG") has been shown to be either a promoter or an inhibitor of neuronal growth depending on factors such as age, type of neuron, and levels of cAMP. P. W. Johnson et al., 3 Neuron 377-385 (1989); G. Mukhopadhyay et al., 13 *Neuron* 757-767 (1994); H. Song et al., 281 *Science* 151-154 (1998). Nogo is a recently-identified inhibitory myelin protein which has three isoforms: Nogo-A, Nogo-B, and Nogo-C. The best-characterized Nogo, Nogo-A, is localized to CNS myelin and is recognized by IN-1. M. S. Chen et al., 403 (6768) *Nature* 434-439 (2000).

5. Cell Signaling

Cells communicate by means of hundreds of kinds of signaling molecules, including proteins, small peptides, amino acids, nucleotides, steroids, retinoids, fatty acid derivatives, and dissolved gases. Many signaling molecules are secreted from the signaling cell by exocytosis. Other signaling molecules are released by diffusion through the plasma membrane, while others remain bound to the cell surface—influencing only the cells that contact the signaling cell.

Target cells respond through a specific protein known as a receptor. The receptor specifically binds the signaling molecule and then initiates a response in the target cell. In many cases, the receptors are transmembrane proteins on the target-cell surface. When such receptors bind extracellular signaling molecules, known as ligands, the receptors become activated and generate a cascade of intracellular signals which alter the behavior of the cell. However, in some cases, the receptors are located inside the target cell. Therefore, the signaling ligand must enter the cell to stimulate activation. Such signaling ligands must be small and hydrophobic such that they are able to diffuse across the plasma membrane.

a. Types of Cell Signaling

Signaling molecules secreted by cells may be carried long distances to work on distant targets. Alternatively, the signaling molecules may act as local mediators, affecting cells only in the immediate environment of the signaling cell. This latter type of signaling is known as paracrine signaling. If paracrine signals are to be delivered only to their proper targets, then the secreted signaling molecules must not be allowed to diffuse too far. Accordingly, they are often either rapidly taken up by neighboring target cells, destroyed by extracellular enzymes, or immobilized by the extracellular matrix.

Short-range signaling is not sufficient to coordinate the behavior of an organism's cells. Specialized cells have evolved which have the ability to convey signals between widely separate parts of the body. The most sophisticated of this type of cells are nerve cells, discussed above. When activated by signals from the environment or from other nerve cells, nerve cells send electrical impulses (action potentials) along its axon. When this impulse reaches nerve terminals at the end of the axon, it stimulates the terminals to secrete a chemical, known as a neurotransmitter. Specialized junctions, known as chemical synapses, ensure that neurotransmitters are delivered to the postsynaptic target cell rapidly and specifically. This signaling is known as synaptic signaling.

Yet another type of specialized signaling cells is endocrine cells. Endocrine cells secrete signaling molecules, known as hormones, into the bloodstream which transports the signal to target cells throughout the body. This type of signaling is relatively slow, compared to synaptic signaling, because endocrine signaling relies on diffusion and blood flow.

In addition to paracrine, synaptic, and endocrine signaling, which concern the influence of one cell type on another, autocrine signaling is yet another way in which cells communicate. In autocrine signaling, cells secrete signaling molecules that can bind back to its own receptors. This behavior is most effective when carried out simultaneously by neighboring cells of the same type, which in turn may encourage groups of identical cells to make the same developmental decisions.

b. Response to Cell Signaling

The particular manner in which a cell reacts to its environment varies. The reaction depends on the set of receptor proteins that the cell possesses which it uses to detect a particular subset of the available signals, and on the intracellular machinery which it uses to integrate and interpret information that it receives. Accordingly, a single signaling molecule may have different effects on different target cells. Different effects may be due to the fact that the target cells have different receptor proteins, or due to the fact that the same signaling molecule may bind to identical receptor proteins, yet produce different responses in different types of target cells. The phenomenon reflects a difference in the internal machinery to which the receptors are coupled.

c. Receptors and Intracellular Proteins Involved in Cell Signaling

All water-soluble signaling molecules and some lipid-soluble signaling molecules bind to specific receptor proteins on the surface of the target cells which they influence. Cell-surface receptor proteins act as signal transducers in that they bind the signaling ligand with high affinity and convert this extracellular event into one or more intracellular signals that alter the behavior of the target cell. Most cell-surface receptor proteins fall within one of three classes: ion-channel-linked receptors, G-protein-linked receptors, or enzyme-linked receptors. The three classes are defined by the transduction mechanism used.

d. Signaling Cascades

As indicated above, many of the molecular cues that guide axonal outgrowth are bifunctional, meaning that they can induce attractive or repulsive responses depending upon various cellular conditions. Among the cellular conditions that induce either attractive or repulsive responses are complex sets of interactions known as "signaling cascades." Signaling pathways are very complex with many different cascades influencing one another. Among the many types of cascades, cyclic nucleotide cascades, phosphorylation cascades, and calcium cascades are representative.

Among the cyclic nucleotide cascades is that of cyclic AMP ("cAMP"). For cAMP to function as an intracellular mediator, its intracellular concentration must be controlled tightly and must be able to change rapidly in response to extracellular signals. cAMP is synthesized from adenosine monophosphate ("AMP") by the enzyme adenylate cyclase, and is destroyed by phosphodiesterases which hydrolize cAMP to adenosine 5'-monophosphate. When cAMP is an intracellular messenger, cell-surface receptors act by altering (usually stimulating) the activity of adenylate cyclase, rather than altering phosphodiester activity.

Activation of adenylate cyclase requires at least three plasma membrane-bound proteins which interact in the following sequence: first, hormone binding to the receptor protein alters the conformation of the receptor, enabling it to bind to and activate the G protein when the two protein molecules collide in the lipid bilayer; second, the latter protein becomes able to bind GTP at its cytoplasmic surface which changes the conformation of the G protein so that it can activate an adenylate cyclase molecule to synthesize cAMP; and third, to complete the cycle, the G protein hydrolyzes the bound GTP to GDP, which returns the cyclase to its original (inactive) state.

The effects of cAMP are normally transient, which indicates that cells must be able to dephosphorylate the proteins that were phosphorylated by cAMP-dependent protein kinases. The dephosphorylation is catalyzed by phosphoprotein phosphatase, which is an enzyme regulated itself by cAMP. Dephosphorylation reactions tend to counteract the protein phosphorylations stimulated by cAMP. However, when the cAMP-dependent protein kinase is activated, it also phosphorylates a specific phophatase inhibitor protein, which is thereby activated. This activated inhibitor protein binds to phosphoprotein phosphatase and inactivates it. By both activating phosphorylase kinase and inhibiting the opposing action of phosphoprotein phosphatase, rises in cAMP have a larger and sharper effect on certain reactions than if the reaction were influenced by cAMP only.

Like cAMP, calcium ("$Ca^{2+}$") is an important cellular regulator which also acts as a second messenger for certain extracellular signaling molecules. Similar to cAMP, the concentration of free $Ca^{2+}$ in the cytosol is normally low. While the total concentration of $Ca^{2+}$ in cells is similar to its concentration outside of the cells, the concentration of $Ca^{2+}$ in the cytosol is more than a thousandfold less because most of the $Ca^{2+}$ in cells is bound to other molecules or sequestered in mitochondria and other intracellular organelles. Therefore, there is an enormous gradient in the concentration of free $Ca^{2+}$ across the plasma membrane that tends to drive $Ca^{2+}$ into the cell.

To maintain this imbalance, any net influx of $Ca^{2+}$ across the plasma membrane must be matched by net efflux across the membrane. This is achieved largely by plasma-membrane-bound $Ca^{2+}$-ATPase which uses the energy to ATP hydrolysis to pump $Ca^{2+}$ out of the cell. $Ca^{2+}$ is also expelled in some cells by other plasma-membrane-bound pumps that act as $Na^+$-driven antiports, coupling the efflux of $Ca^{2+}$ to the influx of $Na^+$.

Cells use the $Ca^{2+}$ gradients to transduce extracellular signals. Just as some cell-surface receptors are functionally coupled to adenylate cyclase molecules, others are coupled to $Ca^{2+}$ channels in the plasma membrane. The transient opening of these channels following receptor activation allows $Ca^{2+}$ to enter the cytosol, where it acts as a second messenger. This mechanism operates in most secretory cells that are activated by extracellular ligands.

Many receptors involved in cell signaling are protein kinases which transfer phosphate groups to target proteins. The best-characterized receptors phosphorylate the target amino acid tyrosine, and are therefore called protein tyrosine kinases. The most common target amino acids for other types of protein kinases are serine or, to a lesser extent, threonine. These protein kinases are therefore known as protein serine/threonine kinases.

It was originally thought that activation of the receptor tyrosine kinase caused other protein tyrosine kinases to be activated, leading farther along the chain to the activation of protein serine kinases. It is now known that components in addition to kinases make up the cascades and that pathways involved in other types of events are triggered. However, the basic concept remains that the signal is amplified as it passes from one component of the pathway to the next, that some components have multiple targets, and that the pathway may branch.

When a ligand binds to the extracellular domain of certain receptors, the catalytic activity of the cytoplasmic domain is activated. Phosphorylation of tyrosine is considered the key event by which these particular receptors function. Two types of events occur following activation of the kinase activity. First, the receptor phosphorylates itself in the cytoplasmic region, known as autophosphorylation. Autophosphorylation is important because it changes the properties of the cytoplasmic domain of the receptor in a way that allows it to bind the next protein in the cascade and because it may further increase the catalytic activity, comprising positive feedback. Second, the receptor phosphorylates target proteins in the cytoplasm. This either activates or inactivates pathways which change the cell phenotype. Phosphorylation of target proteins is a major pathway for moving signals along the cascade, but it is not the only means of activating target proteins. It is believed some proteins that bind to phosphorylated receptors are activated without themselves being phosphorylated.

Some targets that are activated by receptors are themselves kinases. Such targets may, in turn, phosphorylate further kinases, creating a cascade in which a series of phosphorylation events activates successive kinases, ultimately leading to the phosphorylation of target proteins that change transcription or cell structure.

MHC I

Lymphocytes are the agents of antigenic specificity in the immune response and may be divided into two groups. The first group, B cells, produces immunoglobulins ("Igs"). The second group, T cells, performs various functions, including helping B cells, producing delayed-type hypersensitivity reactions, and killing virus-infected cells. B cells possess only one source of specificity, the Igs. T cells, on the other hand, possess two sources of specificity: T cell receptors ("TcRs") and major histocompatibility complex molecules (MHC) glycoproteins. The present invention relates to this latter source of specificity for T cells.

The function of MHC molecules is to bind peptide fragments derived from pathogens and display them on cell surfaces for appropriate T cell recognition. The MHC is a series of more than one hundred genes in humans that codes for protein molecules responsible for cell-cell recognition and interaction. Currently, it is believed that there are three structurally distinct, yet related families or "classes" of MHC molecules. Class I MHC molecules present antigens to T cells that express the CD8 cell-surface glycoprotein. Class II MHC molecules present antigens to T cells that express the CD4 cell-surface glycoprotein. Class III MHC molecules code for certain complement components. The present invention relates more specifically to Class I MHC molecules.

MHC, also known as human leukocyte antigens (HLA), is polygenic. There are several MHC Class I genes. These genes encode proteins with different ranges of peptide-binding specificities. In addition, the MHC is highly polymorphic, as there are multiple alleles of each gene. In fact, the MHC genes are the most polymorphic genes known.

MHC I is expressed by all nucleated cells of the body, with the exception of gametes, and a very limited expression by neurons (see below). MHC I binds intracellular peptides and presents them on the cell surface to be surveyed by CD8+T cells (also known as cytotoxic T lymphocytes). The MHC I complex consists of a heavy chain, β2-microglobulin (β2 m) and the bound peptide that it presents. Zijlstra et al., 344 *Nature* 742-6 (1990); Williams et al., 142 *Journal of Immunology* 2796-806 (1989); Heemels and Ploegh, 64 *Annual Review of Biochemistry* 463-91 (1995); Viret and Janeway, Jr., 1 *Review of Immunogenetics* 91-104 (1999); Natarajan et al., 1 *Review of Immunogenetics* 32-46 (1999).

The heavy chains are highly polymorphic in the cleft region that binds intracellular peptides for display to T cells. Consequently, different MHC I molecules bind different intracellular peptides. To supply the MHC I molecules with peptide, intracellular transporters known as "TAP" are required. Heemels and Ploegh, 1995; Jackson and Peterson, 9 *Annual Review of Cell Biology* 207-35 (1993).

Humans possess three main Class I MHC genes: HLA-A, HLA-B, and HLA-C. Because of this, every individual will express at least three different Class I MHC proteins. More than one hundred alleles of some Class I and Class II loci exist, each allele present at rather high frequencies in the population. Due to the extensive polymorphism at each locus, there exists the potential to double the number of distinct MHC molecules expressed in an individual. This increases the diversity already available through polygeny, the existence of multiple functionally equivalent loci.

There are many Class I MHC genes that encode variants of these proteins that exhibit minimal polymorphism. The function of most of these has not yet been determined. These genes are linked to the Class I region of the MHC, and have been termed Class IB MHC genes. Like Class I MHC genes, these genes encode $\beta_2$-microglubulin-associated cell surface molecules.

Peptides bind to Class I MHC molecules via specific anchor residues. These residues are peptide amino acid side chains bound in pockets lining the peptide-binding groove. The polymorphism of Class I MHC molecules affects the amino acids lining these pockets, and, therefore, their binding specificity. As a result, the anchor residues of peptides that bind to each allelic variant are different. The sequence motif, or set of anchor residues that allows binding to a given Class I MHC molecule, makes it possible to identify peptides within a protein that can potentially bind the appropriate MHC molecule.

The level of expression of human classical Class I MHC genes is considerably varied, ranging from total absence (e.g., in trophoblast cells) to high (e.g., in lymphoid tissues or lymphoblastoid cell lines). This variation in expression reflects the highly regulated processes that govern transcription, translation, and transport of each locus product. It has been shown that in primary human melanomas, as well as melanoma cell lines, Class I MHC expression is often downregulated in a B locus-specific manner. S. Agrawal and M. Kishore, 9 *Journal of Hematotherapy & Stem Cell Research* 795-812 (2000).

It has recently been determined that CIITA and RFX play a role in the regulation of Class I MHC expression. The implication of this determination is that CIIT and RFX are involved in a regulatory pathway shared by Class I and Class II MHC genes. van den Elsen P J et al., 19 *Immunology Today* 308-312 (1998). Because reduced levels of Class I MHC transcripts can be found in both IFN-γ-unstimulated and stimulated RFX-deficient cell lines, RFX plays a role in Class I MHC genes' constitutive and IFN-γ-mediated expression.

Tumors generally show low Class I MHC expression and increased tumorogenic potential, which may be benefited from up-regulation of expression of these cell surface molecules. A. R. Vora et al., 76 *British Journal of Cancer* 836-844 (1997). Class I MHC gene expression has been observed to be inducible by several cytokines, including alpha and gamma interferons and interleukins. P. A. Burke and K. Ozato, 4 *The Year in Immunology* 23-40 (1989); B. David-Watine, 11 *Immunology Today* 286-292 (1990). In addition to cytokines, other modulators, such as the nucleotide analogues 5-azacytidine cytosine arbinoside, 5-fluoracil, and plant alkaloid uricristine, may have the same effect. O. Yano et al., 6 *Journal of EMBO* 3317-3324 (1987). Other substances, such as retinoids and vitamin D3, are able to induce Class I MHC expression. A. S. Baldwin and P. A Sharp, 85 *Proceedings of the National Academy of Sciences U.S.A.* 723-727 (1988).

Many receptors for growth hormones and neurotransmitters are coupled to enzymatic effector systems regulating the production of second messengers. K. Kawakami et al., 85 *Proceedings of the National Academy of Sciences USA* 4700-4704 (1988). Among these are the p21ras-mediated MAP kinase pathway leading to activation of the jun transcription factor and the cAMP-dependent protein kinase A (PKA)-mediated pathway putatively involved in the activation of many transcription factors. These include IL-1-induced activation of NF-kB and the cAMP-responsive element binding-CREB proteins. PKA activity and the transcription factors activated by it are involved in basal and induced expression of many genes, including the MHC. T. Nakamura et al., 10 *Molecular Cell Biology* 3700-3708 (1990); A. Israel et al., 8 *Journal EMBO* 3793-3800 (1989).

Transactivation of Class I MHC genes is mediated by two groups of juxstaposed cis-acting elements that can be viewed as regulatory modules. The upstream-most module consists of the enhancer A and ISRE and mediates the constitutive and cytokine induced expression. The S-X-Y module is important to consitutive and CIITA-mediated transactivation. These modules are absent in antigen G expression. There may be some regulatory sequences in the proximal promoter region (−1500 bp) and in the first five intronic sequence, in the regulation of Class I MHC expression of HLA-G. S. J. Gobin et al., 1 *Seminars in Cancer Biology* 55-59 (1999).

HIV-1 specifically and strongly decreases the activity of the Class I MHC gene promoter up to 12-fold. The HIV-I proteins Vpu and Nef have been shown to decrease Class I MHC expression. Vpu induces rapid loss of Class I heavy chains in the ER of peripheral blood leukocytes that are depleted of CD8 cells.

Interferons are able to up-regulate expression of Class I MHC genes. Type I and type II interferons share the ability to alter the pattern of expression of a variety of IFN-inducible genes by regulating transcriptional activities. IFN-gamma up-regulates gene expression of several proteasomal subunits as well as the proteasome regulator PA28.

In addition to modulation by biological molcules, several synthetic compounds have been shown to up-regulate Class I MHC expression. Such synthetic compounds include analogs of pyridines, vitamins, neurotransmitters, and several chemotherapeutic agents used in cancer therapy. Of the nucleotide analogs, 5' azacytidine is a significant modulator of Class I MHC gene expression. Generally, it has been found to induce up-regulation of Class I MHC gene expression in the absence of differentiation. Its affects are augmented when combined with IFN-gamma.

Mice have three heavy chain loci; D, K, and L, each of which are highly polymorphic. Each mouse inherits two D, L, and K alleles, and expresses these six genes in most of their cells. Through inbreeding, mouse strains that are homozygous for specific MHCI alleles are readily available (e.g., C57B16 mice are $D^b, K^b, L^b$, while SJL mice are $D^s, K^s, L^s$).

The TcR gene undergoes rearrangement in T cells to create a vast array ($>10^{15}$) of different TcRs, just as immunoglobin genes undergo rearrangement in B cells. Each CD8+T cell expresses a single rearranged TcR gene. Viret and Janeway, Jr., 1999; Berg and Kang, 13 *Current Opinions in Immunology* 232-41 (2001); Nemazee, 18 *Annual Review of Immunology* 19-51 (2000). Generally, only $1/10^5$-$1/10^6$ of unactivated CD8+T cells possess a TcR that is able to recognize a specific peptide/MHCI complex. A T cell that recognizes a peptide bound by a particular MHC I type (e.g., $D^b$) will not recognize the same peptide bound to another MHC I type (e.g., $D^s$)—i.e., its recognition is "MHC I-restricted."

CD8+T cells with TcRs that recognize self-peptides presented by MHC I are generally eliminated. Viret and Janeway, 1999; Matzinger, 12 *Annual Review of Immunology* 991-1045 (1994). As a result, if a CD8+T cell binds a MHC I/peptide complex, it is likely that the cell is producing foreign proteins (e.g., from a virus). The TcR lacks a domain that can send an intracellular signal when it binds MHC I/peptide. 25 Instead, this function is carried out by the CD3 complex, which associates with the TcR (FIG. 4). When the TcR binds a MHC I/peptide complex, the cytoplasmic domains of the proteins comprising the CD3 complex, and particularly the CD3ξ chains, are phosphorylated. This leads to the activation of Zap-70 (van Leeuwen and Samelson, 11 *Current Opinions in Immunology* 242-8 (1999); Bromley et al., 19 *Annual Review of Immunology* 375-96 (2001)), and a cascade of intracellular signaling events that lead to T cell proliferation, cytokine secretion, inactivation, or apoptosis.

It is generally accepted that CNS neurons are immune privileged cells in which immune functions appear to be restricted. Thus, it was long thought that CNS neurons, unlike almost all other cells in the mammalian body, expressed little or no MHC I molecules that are necessary to present intracellular proteins to the immune system. E. Joly et al., 253 *Science* 1283-5 (1991); L. A. Lampson, 32 *Microscience Research Technology* 267-85 (1995); H. Neumann et al., 269 *Science* 549-52 (1995); H. Neumann et al., 185 *Journal of Experimental Medicine* 305-16 (1997); O. Lidman et al., 11 *European Journal of Neuroscience* 4468-72 (1999). This phenomenon was believed to be an adaptation for survival based on the inability of neurons to replicate. Recently, however, MHC I has been shown to be expressed on CNS neurons. R. A. Corriveau et al., 21 *Neuron* 505-20 (1998); G. S. Huh et al., 290 *Science* 2155-9 (2000). In particular, it was shown that neurons express MHC I during embryonic brain development in the cat and in the rat, and the timing of this expression is associated temporally with synaptogenesis. R. A. Corriveau, 21 *Neuron* 505-520 (1998). This posed the question as to what role MHC I played in neuronal guidance.

In view of the numerous causes and drastic symptoms associated with neuron loss and neuron injury, as exemplified by the previous discussion, and in view of the drawbacks and uncertainties associated with the known attempts at treatment, it should be apparent that there exists a need in the art for an effective way to modulate neuron outgrowth.

SUMMARY OF THE INVENTION

The present invention includes a method for enhancing neurite outgrowth, which includes contacting neural cells with an agent which inhibits activity of a major histocompatibility complex Class I (MHC I) molecule, wherein the agent is present in an amount which is effective for enhancing neurite outgrowth, and wherein the neural cells comprise neurons. The cells may be present in the patient or subject, which preferably includes mammals. The neurons are preferably CNS neurons. MHC I may be membrane bound or soluble. Soluble or membrane bound MHC I may come from immune cells may come from immune cells that migrate into damaged areas. Immune cells, such as macrophages, T cells, B cells, dendritic cells, and microglia, may also be sources of soluble and membrane bound MHC I that locally limit repair responses. Damage also induces neurons and other cells to release cytokines such as IFN-γ, which then induce MHC I on neurons.

The activity of the MHC I includes the binding of MHC I to a ligand, including an antibody, an MHC I analog, and an MHC I fragment or peptide. The activity may also be the binding of MHC I to its receptor, or the presentation of antigens, the expression of MHC I, or any intracellular signaling cascade induced by MHC I. In a preferred embodiment, the intracellular signaling cascade is a phosphorylation cascade. The agent includes pharmaceutical compounds, peptides or polypeptides and nucleic acids.

The invention also relates to a method for treating neural damage, which includes contacting neural cells with an agent which inhibits activity of a major histocompatibility complex Class I (MHC I) molecule, wherein the agent is present in an amount which is effective for enhancing neurite outgrowth, and wherein the neural cells comprise neurons. The neural damage may be caused by injury, trauma or disease, particularly an injury such as stroke and particularly a neurodegenerative disease such as Alzheimer's Disease, Parkinson's Disease, or Huntington's Disease.

The invention also relates to a method for identifying agents which reduce MHC I-induced inhibition of neurite outgrowth, which includes the steps of:
(a) contacting neural cells with the agent;
(b) measuring a level of MHC I or MHC I activity in the presence of the agent;
(c) measuring increased neurite outgrowth in the presence and absence of the agent; and
(d) correlating decreased MHC I activity and increased neurite outgrowth in the presence of the agent with the ability of the agent to reduce MHC I-induced inhibition of neurite outgrowth.

The invention also relates to pharmaceutical compositions for treating neural damage, including:
(a) an agent which inhibits activity of a major histocompatibility complex Class I (MHC I) molecule, wherein said agent is present in an amount which is effective for enhancing neurite outgrowth; and
(b) a pharmaceutically acceptable carrier.

BRIEF DESCRIPTION OF THE DRAWINGS

FIG. 1A shows retinal explants extending processes toward wt thalami (Th). FIG. 1B shows that retinal explants do not extend processes toward thalami from transgenic mice which express MHC I on their neurons. FIG. 1C shows group data of wt retinal outgrowth toward a wt thalamus (open bar), or a MHC 1-tg thalamus (black bars), in the absence, or presence of different antibodies. The relative retinal extension towards the thalamus was scored by 2 blinded individuals on a scale of 0-100 (n≧8/group). The mean retinal outgrowth score in control co-cultures (with wt thalami) was adjusted to be 100, and all other scores were adjusted by the same factor. Data shown are the mean relative outgrowth±standard error of the mean (SEM). Retinal neurite outgrowth toward a MHC I-tg thalamus was reduced compared to growth towards a wt thalamus (p<0.001 by Student's t-test). Addition of a MHC I $D^b$-specific monoclonal antibody, but not anti-MHC I $D^k$, anti-GAD, or total mouse IgG2a, to the culture rescued axonal outgrowth. The difference between the experimental group (with anti-$D^b$) and control groups (with, or without, other antibodies) was statistically significant (p<0.005 in Student's t-test). FIG. 1D shows retinal neurite outgrowth toward a wt thalamus was unaffected by the addition of conditioned media (cm) from wt thalamic cultures (no treatment bar vs. wt cm bar). In contrast, transfer of conditioned media from MHC I-tg thalamic cultures had a statistically significant inhibitory effect on neurite outgrowth from wt retinas (tg cm bar) (p<0.005 by Student's t-test). Addition of anti-MHC I $D^b$, but not anti-MHC I $D^k$, significantly rescued neurite outgrowth in co-cultures exposed to MHC I-tg conditioned media (p<0.005 in Student's t-test).

FIG. 2A shows representative cultures of retina (alone) incubated with media from COS cells transfected with control plasmid. FIG. 2B shows representative cultures of retina (alone) incubated with media from COS cells transfected with a plasmid encoding a MHC I $D^b$ that lacks its membrane anchor. FIG. 2C shows group data showing significantly reduced retinal axonal outgrowth in the presence of rMHC I (p =0.002 by 2-tailed T test). Addition of Rp-cAMPs (20 uM) to cultures containing rMHC I prevented the inhibitory action of rMHC I. Images were analyzed using NIH Image software and shown as the mean outgrowth of the longest neurite in the cultures (micrometers +/−SEM.)

FIG. 3A shows representative AChE stained sections from lesioned wt mice. FIG. 3B shows representative AChE stained sections from MHC I-tg mice. The AChE staining patterns on unlesioned side of wt and MHC I-tg mice are indistinguishable. However, compensatory cholinergic sprouting responses can be readily seen in the molecular layer (ML) on the lesioned side of wt, but not MHC I-tg mice. FIG. 3C shows the increase in AChE positive fibers in the molecular layer of the lesioned side of wt mice under higher power. FIG. 3D shows the increase in AChE positive fibers in the molecular layer of the unlesioned side of wt mice under higher power. FIG. 3E shows the analysis of density of AChE staining in the dentate gyrus using NIH Image analysis software. Data shown are the mean ratio of AChE staining in the molecular layer of the dentate gyrus on the lesioned/unlesioned side (+/−SEM). The average density of 5-10 sections per mouse was used for statistical analysis (N=6-7 mice per group at each time point). FIG. 3F shows MHC I-tg mice (black circles) display a deficit in recovery of spontaneous alteration behavior compared to wt mice (open boxes) following perforant path lesioning. Spontaneous alternation behavior was performed as previously described. Scheff and Cotman, 21(2) *Behavioral Biology* 286 (1977).

DETAILED DESCRIPTION OF THE PREFERRED EMBODIMENTS OF THE INVENTION

Figure 1:
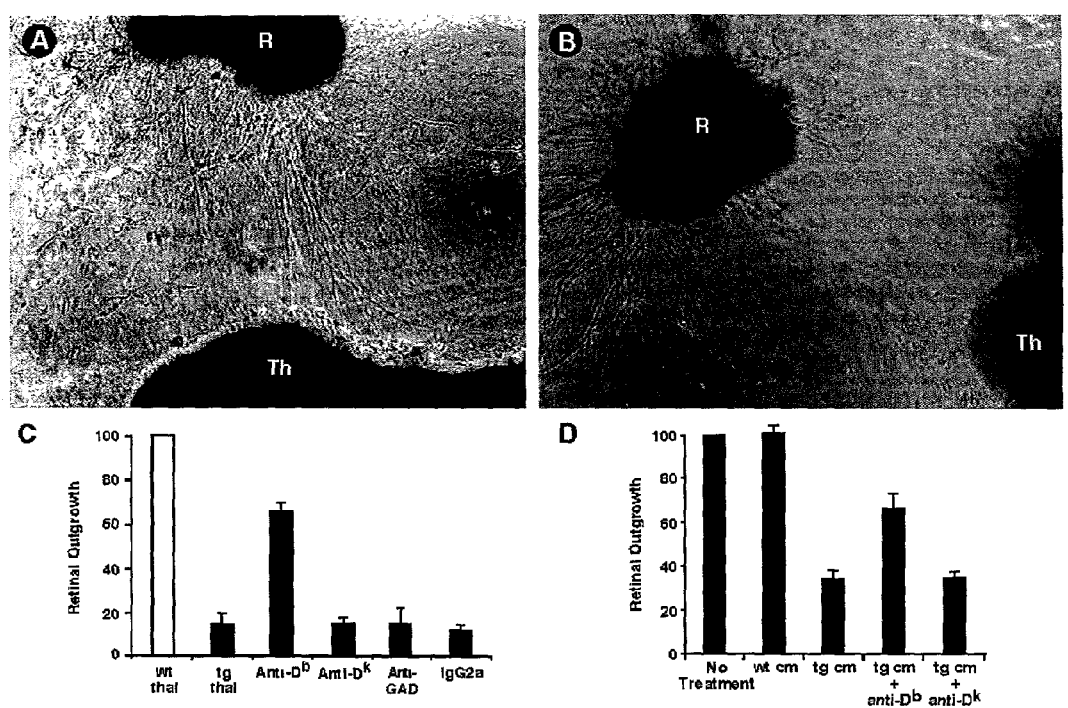
FIG. 1 shows representative co-cultures of wild type (wt) retinal explants (R).

In accordance with the present invention there may be employed conventional molecular biology, microbiology, immunology, and recombinant DNA techniques within the skill of the art. Such techniques are explained fully in the literature. See, e.g., Sambrook et al., "*Molecular Cloning: A Laboratory Manual*" (3$^{rd}$ edition, 2001); "*Current Protocols in Molecular Biology*" Volumes I-III (Ausubel, R. M., ed. (1999 and updated bimonthly)); "*Cell Biology: A Laboratory Handbook*" Volumes I-III (J. E. Celis, ed. (1994)); "*Current Protocols in Immunology*" Volumes I-IV (Coligan, J. E., ed. (1999 and updated bimonthly)); "*Oligonucleotide Synthesis*" (M. J. Gait, ed. (1984)); "*Nucleic Acid Hybridization*" (B. D. Hames & S. J. Higgins, eds. (1985)); "*Transcription And Translation*" (B. D. Hames & S. J. Higgins, eds. (1984)); "*Culture of Animal Cells, 4$^{th}$ Edition*" (R. I. Freshney, ed. (2000)); "*Immobilized Cells And Enzymes*" (IRL Press, (1986)); B. Perbal, "*A Practical Guide To Molecular Cloning*" (1988); *Using Antibodies: A Laboratory Manual: Portable Protocol No. I*, Harlow, Ed and Lane, David (Cold Spring Harbor Press, 1998); *Using Antibodies: A Laboratory Manual*, Harlow, Ed and Lane, David (Cold Spring Harbor Press, 1999); "*G Protein-Coupled Receptors*" (T. Haga, et al., eds. (1999)).

Unless otherwise stated, the following terms used in the specification and claims have the meanings given below:

"Acetylcholinesterase" refers to an enzyme that metabolizes acetylcholine.

"AChE" is an abbreviation used interchangeably with acetylcholinesterase.

"Administer" and "Administering" mean introducing a compound or composition to an organism, or a cell or group of cells in culture.

"Ameliorate" is defined as a lessening of the detrimental effect of the condition suffered by the patient.

"Animal" is meant to include mammals, particularly such mammals as primates, bovines, canines, felines, ovines, porcines, and rodents, etc. Rodents include, inter alia, mice, hamsters, rabbits, and guinea pigs. However, animal can include any eukaryote.

"Antibody" is intended to refer broadly to any immunologic binding agent, such as IgG (including IgG1, IgG2, IgG3, and IgG4), IgM, IgA, IgD, IgE, as well as antibody fragments. Antibody in the broadest sense covers intact monoclonal antibodies, polyclonal antibodies, as well as biologically active fragments of such antibodies and altered antibodies, including chimeric antibodies (U.S. Pat. No. 4,816,567).

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

By "monoclonal antibody" is meant an antibody obtained from a population of substantially homogenous antibodies, i.e., the individual antibodies comprising the population are identical except for the possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In addition to their specificity, monoclonal antibodies are advantageous in that they are synthesized by the hybridoma culture, uncontaminated by other immunoglobulins. The modifier "monoclonal" indicates the character of the antibody as being obtained from a substantially homogenous population of antibodies, and is not to be construed as requiring production of the antibody by any particular method. For example, the monoclonal antibodies to be used in accordance with the present invention may be made by the hybridoma method first described by Kohler et al., 256 Nature 495-7 (1975), or may be made via recombinant DNA methods. See U.S. Pat. No. 4,816,567 to Cabilly et al. The monoclonal antibodies may also be isolated from phage antibody libraries using the techniques described, for example, in Clackson et al., 352 Nature 624-8 (1991) and Marks et al., 222 Journal of Molecular Biology 581-97 (1991). A monoclonal antibody typically displays a single binding affinity for any antigen with which it immunoreacts. A monoclonal antibody may contain an antibody molecule having a plurality of antibody combining sites, each immunospecific for a different antigen; e.g., a bispecific (chimeric) monoclonal antibody.

"Antisense," as used herein, refers to the modulation of function of a target nucleic acid by compounds which specifically hybridize to it. Antisense compounds are commonly used as research reagents and diagnostics. For example, antisense oligonucleotides are often used by those of ordinary skill to determine the function of a particular gene because such oligonucleotides are able to inhibit gene expression with great specificity. Antisense oligonucleotides are also used as therapeutic moities in the treatment of disease states in mammals.

"Blood brain barrier" refers to the tightly packed wall of endothelia that separates the circulatory system from central nervous system cells.

A "cell line" is a clone of a primary cell that is capable of stable growth in vitro for many generations.

"Central Nervous System" refers to the vertebrate brain and spinal cord.

"CNS" is an abbreviation used interchangeably with central nervous system.

A "clone" is a population of cells derived from a single cell or common ancestor by mitosis.

"Cyclic Adenosine Monophosphate" is a nucleotide that is generated from Adenosine triphosphate ("ATP") in response to hormonal stimulation of cell-surface receptors. Cyclic adenosine monophosphate acts as a signaling molecule by activating A-kinase. Cyclic adenosine monophosphate is hydrolyzed to adenosine monophosphate by a phosphodiesterase.

By "cAMP" is meant the abbreviation, used interchangeably, with cyclic adenosine monophosphate.

"Cyclic Guanosine Monophosphate" is a nucleotide which acts as a signaling molecule and is a close relative of cAMP.

By "cGMP" is meant the abbreviation, used interchangeably, with cyclic guanosine monophosphate.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Two amino acid sequences are "substantially homologous" when at least about 70% of the amino acid residues (preferably at least about 80%, and most preferably at least about 90 or 95%) are identical, or represent conservative substitutions.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

By "expression vector" is meant the functional definition of any DNA sequence which is capable of effecting expression of a specified DNA code in a suitable host. At present, such vectors are frequently in the form of plasmids, thus "plasmid" and "expression vector" are often used interchangeably. However, the invention is intended to include such other forms of expression vectors which serve equivalent functions and which may become known in the art. Typically, an expression vector is a nucleic acid molecule comprising: (1) a promoter and other sequences (i.e., leader sequences) necessary to direct expression of a desired gene or DNA sequence; and (2) the desired gene or DNA sequence. Optionally, the nucleic acid molecule may comprise an Adenine-rich ("poly A tail") signal sequence to enhance the stability of the gene transcript and/or to increase gene transcription and expression.

"Ganglion Cell Layer" is the layer of neuronal cells in the mammalian retina whose axons form the optic nerve.

"GCL" is an abbreviation used interchangeably for ganglion cell layer.

"Gene" means the segment of DNA involved in producing a polypeptide chain. It includes regions preceding and following the coding region, as well as intervening sequences (i.e., introns) between the coding sequences ("exons").

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

By "host cells" is meant cells that have been recombinantly transformed with vectors constructed using recombinant DNA techniques. In describing processes for isolation of antibodies from recombinant hosts, the terms "cell," "cell culture," and "cell line" are used interchangeably to denote the source of the antibody, unless it is clearly specified otherwise. In other words, recovery of antibody from the "cells" may mean either from spun down whole cells, or from the cell culture containing both the medium and the suspended cells.

"Lateral Geniculate Nucleus" refers to the area of the brain that serves as a relay station in the pathway from the eye to the cerebral cortex. Optic nerve fibers arise from ganglion cells in the retina and end on cells in the lateral geniculate nucleus whose axons, in turn, project through the optic radiation to the cerebral cortex.

"LGN" is an abbreviation used interchangeably for lateral geniculate nucleus.

"Mammal" refers to primates, bovines, canines, felines, ovines, porcines, and rodents, etc. Rodents include mice, hamsters, rabbits, and guinea pigs.

"MHC I" is an abbreviation used interchangeably for Major Histocompatibility Complex Class I.

By "modulating" or "regulating" is meant the ability of an agent to alter from the wild-type level observed in the individual organism the level of expression of a gene.

"Nerve Growth Factor" refers to one of several secreted factors which are required for the differentiation of neuronal precursors into mature neurons, for the continuing survival of neurons, and for the programming of neurotransmitters produced by each cell.

By "neural cell" is meant to include any cell which may be present in tissue in the nervous system at any time, including neurons, glial cells, endothethial cells, and cells of the immune system.

"NGF" is an abbreviation for nerve growth factor, that may be used interchangeably with the full term.

"Netrins" are a family of secreted proteins that bind to two receptor types, DCC and UNC, and can induce attractive or repulsive responses depending on the type of receptor expressed.

"Neurotrophins" are factors involved in axonal growth that bind ligand-specific receptor tyrosine kinases which activate multiple intracellular signaling pathways.

"Neutralize" refers to the act of countering the action of something such that it produces no net effect.

"Nucleic acid" includes DNA, genomic DNA, RNA, mRNA and cDNA. The preferred nucleic acids of the invention include those that encode immunoglobulins or fragments thereof which recognize MHC I.

"Oligonucleotide" means an oligomer or a polymer of ribonucleic acid (RNA) or deoxyribonucleic acid (DNA) comprised of two or more ribo- or deoxyribonucleotides, preferably more than three. Its exact size will depend upon many factors which, in turn, depend upon the ultimate function and use of the oligonucleotide. Oligonucleotides composed of naturally-occurring nucleobases, sugars and covalent internucleoside linkages as well as oligonucleotides having non-naturally-occurring portions which function similarly are included in this definition. Modified or substituted oligonucleotides are often preferred over native oligonucleotides because of enhanced cellular uptake, enhanced affinity for nucleic acid targets, increased stability in the presence of nucleases, and other desired properties.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

An "origin of replication" refers to those DNA sequences that participate in DNA synthesis.

By "patient" is meant any mammal in need of treatment.

"Perforant Path" refers to the main cortical afferent pathway to the hippocampus projecting from the entorhinal cortex to the dentate gyrus.

"Peripheral Nervous System" refers to neural tissue other than the brain and spinal cord. "PNS" is the abbreviation, used interchangeably, for peripheral nervous system.

The phrase "pharmaceutically acceptable" refers to molecular entities and compositions that are physiologically tolerable and do not typically produce an allergic or similar untoward reaction, such as gastric upset, dizziness and the like, when administered to a human.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background.

Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

By "purified" and "isolated" is meant, when referring to a polypeptide or nucleotide sequence, that the indicated molecule is removed from its natural state, i.e., not as it occurs in nature. This differs from the use of these terms as applied to other substances, where the term "purified" as used herein preferably means at least 75% by weight, more preferably at least 85% by weight, and still more preferably at least 95% by weight, and most preferably at least 98% by weight pure.

By "regenerate" is meant, for example, the act of a nerve regrowing once it has been cut.

A "replicon" is any genetic element (e.g., plasmid, chromosome, virus) that functions as an autonomous unit of DNA replication in vivo; i.e., capable of replication under its own control.

As used herein, the terms "restriction endonucleases" and "restriction enzymes" refer to bacterial enzymes, each of which cut double-stranded DNA at or near a specific nucleotide sequence.

"Semaphorins" are a family of secreted and membrane-bound proteins that act as repulsive guidance cues to axonal growth cones.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "sprout" refers to, for example, the genesis of a new axon from a location that, immediately prior, had no such axon.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Superior Colliculus" refers to nuclei in the mammalian brain stem involved in visual processing.

"SC" is an abbreviation used interchangeably with superior colliculus.

By "therapeutically effective amount" is meant an amount of sufficient quantity to prevent or ameliorate the condition suffered by the patient. The phrase "therapeutically effective amount" is preferably used herein to mean an amount sufficient to prevent, and preferably reduce by at least about 30 percent, more preferably by at least 50 percent, most preferably by at least 90 percent, a clinically significant change in some feature or pathology such as for example, elevated blood pressure, fever or white cell count as may attend its presence and activity.

"Transcriptional and translational control sequences" are DNA regulatory sequences, such as promoters, enhancers, polyadenylation signals, terminators, and the like, that provide for the expression of a coding sequence in a host cell.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

"Transgenic" refers to an organism whose genome has been modified by externally-applied new DNA.

"Transcriptional and translational control sequences" are DNA regulatory sequences, such as promoters, enhancers, polyadenylation signals, terminators, and the like, that provide for the expression of a coding sequence in a host cell.

A "vector" is a replicon, such as plasmid, phage or cosmid, to which another DNA segment may be attached so as to bring about the replication of the attached segment.

"Wild Type" means the genotype or phenotype that is found in nature or in the standard laboratory stock for a given organism.

The present invention relates to methods and compositions for treating neural damage caused by injury or disease, by enhancing neural outgrowth and/or repair responses in the nervous system. Preferably, the methods are conducted on CNS cells.

The invention also includes an assay system for screening of potential drugs or agents which are effective to modulate neurite outgrowth by interfering with the ability of MHC I to inhibit neurite outgrowth. In one instance, a sample of neurons expressing MHC I can be tested in the presence and absence of the test drug, and the relative effects of the presence of the test drug on the two cultures can be assessed. Where neurite outgrowth is enhanced in the presence of the test drug, one correlates those results with the ability of the test drug to enhance neurite outgrowth, and/or lessen the ability of MHC I to inhibit neurite outgrowth.

The assay system could also be adapted to identify drugs or other entities that are capable of binding to the MHC I and/or other factors or proteins in the cell which are associated with the actions of MHC I. Such drugs may be useful in treating neural damage, preferably damage to neurons, and more preferably damage to CNS neurons. The drugs so identified may also be useful in treating diseases of the nervous system, preferably diseases which affect neurons, and more preferably diseases of CNS neurons. In one embodiment of the invention, the drugs may be useful for treating neurodegenerative diseases, such as Alzheimer's Disease, Parkinson's Disease, and other neurodegenerative diseases known to those of skill in the art.

The invention also relates to methods of diagnosing a disease known to be associated with the inhibitory action of MHC I on neurite outgrowth, by treating neurons of a patient or subject, either in vitro or in vivo, with a drug or agent identified in accordance with an embodiment of the invention. Where the neurite outgrowth of the neurons is enhanced, or the neural status of a patient is improved in the presence of the drug or agent, one can attribute the symptoms of the disease to a disease associated with the inhibitory action of MHC I on neurite outgrowth.

The invention also relates to the treatment and/or prevention of neural injury or neural disease, by treating neurons of a patient or subject, with an amount of a drug or agent identified in accordance with an embodiment of the invention effective to reduce or alleviate the symptoms of that injury or disease.

In yet a further embodiment, the invention relates to compositions which are effective to reduce or alleviate MHC I-induced inhibition of neurite outgrowth. Such compositions may include ligands of MHC I which block further binding or activity of the MHC I molecule. In one embodiment, the ligand may be an antibody. In another embodiment, the composition may include a molecule which modulates cellular activity or pathways within the cells which are induced by MHC I.

In one embodiment, the composition may include a molecule which down-regulates levels of MHC I. Examples of such molecules include viral proteins, for example the Nef protein of human immunodeficiency virus, (Agrawal and Kishore, December 9(6) *Journal of Hematotherapy and Stem Cell Research* 795-812 (2000)) and human cytomegalovirus (HCMV) US3 and US6. It has been shown that HCMV US3 physically associates with both trophoblast class I MHC species, retaining them in the endoplasmic reticulum and that HCMV US6 inhibits peptide transport by TAP and thus specifically the intracellular rafficking of class I molecules. Jun et al., January 15 164(2) *Journal of Immunology* 805-11 (2000).

In addition, some cytokines may also down-regulate MHC I, including TGF- (Ma and Niederkorn, October 86(2) *Immunology* 263-9 (1995)) and interleukin-10 (IL-10). Mosmann, 56 *Advances in Immunology* 1 (1994). There are also several negative regulators of Class I MHC expression. For example, several immunosuppressants, like cyclosporin A and FK 506, are known to block the $Ca^{2+}$ dependent pathways of signal transduction. They are known to inhibit expression of IL-2 beside abrogating the activity of $Ca^{2+}$ dependent transcription factors such as NF-AT, NF-IL6, AP-1 and NF-kB. S. I. Tanaguchi et al., 12 *Molecular Endocrinology* 19-33 (1998). Immunosuppressants inhibit constitutive and induce Class I MHC expression. This property is especially valuable for transplant surgery. Alpha-fetoprotein has been reported to inhibit macrophage Ta expression in mouse. This may indicate an immunoregulatory role of this protein in maintaining the fetal allograft. Prostaglandins have been shown to inhibit the expression of MHC antigens.

In another embodiment, the composition may include a molecule which interferes with molecules which are part of the MHC I complex or are active in the process of MHC I's presentation of antigens. It is known that MHC-I molecules present cellular and pathogen-derived peptides to antigen-specific receptors on CD8 T cells. The initial steps of MHC-I biosynthetic and transport pathways are well characterized. Proteolysis of intracellular proteins generates peptides, which are actively transported into the endoplasmic reticulum (ER) for assembly with MHC-I. Ploegh, 280 *Science* 248-253 (1998);York and Rock, 14 *Annual Review of Immunology* 369-396 (1996). Key actors include the multicatalytic proteasome; ER chaperones (calnexin and calreticulin); TAPs (transporters associated with antigen processing), which translocate peptides across the ER membrane; and tapasin, a protein which bridges MHC-I and TAPs. MHC-I trimolecular complexes, which consist of a highly polymorphic heavy chain, 2-microglobulin, and the antigenic peptide, are then routed through the Golgi to the cell surface. Thus, molecules which interfere with the interaction of MHC I with, or the expression of one or more of these molecules, e.g., beta-2 microglobulin, calnexin, calreticulin, TAPs and/or tapasin are also useful in accordance with the present invention.

In another preferred embodiment, the molecule may be a cAMP analog or antagonist. Specific examples of such an analog or antagonist include forskolin, Sp-5,6-DCI-cBIMPS, 6-MAH-cAMP, Rp-8-HA-cAMPS, 8-HA-cAMP, Sp-8-CPT-cAMPS, 5,6-DCI-cBIMP, Rp-8-CPT-cAMPS, 6-MBC-cAMP, 8-CPT-cAMP, 8-Mant-cAMP, Rp-8-Br-MB-cAMPS, 8-Fluo-cAMP, 8-BT-cAMP, 5,6-DM-cBIMP, 6-Phe-cAMP, 8-MABA-cAMP, 6-Bn-cAMP, DB-cAMP, Sp-8-PIP-cAMPS, Rp-8-PIP-cAMPS, 8-NBD-cAMP, 8-PIP-cAMP, Rp-2'-O-MB-cAMPS, 2'-O-MB-cAMP, 6-Bnz-cAMP, Sp-8-Br-cAMPS, Sp-8-CI-cAMPS, $N^6$-MB-cAMP, Rp-8-Br-cAMPS, Rp-8-CI-cAMPS, 2-Aza-ϵ-cAMP, 8-$N_3$-cAMP, 8-Br-cAMP, ϵ-cAMP, 8-AHA-cAMP, 6-CI-cPuMP, 2-CI-cAMP, 8-CI-cAMP, Sp-cAMPS, Rp-cAMPS, cTuMP, Sp-8-OH-cAMPS, 8-ADOA-cAMP, 8-MA-cAMP, cPuMP, 2'-dcAMP, Rp-8-OH-cAMPS, and 8-OH-cAMP.

In yet another embodiment, the composition may include a nucleic acid, for example an antisense molecule or ribozyme, which inhibits the expression of MHC I. Such a composition may be provided to the neurons either ex vivo or in vivo through gene therapy or nucleic acid vaccination, such as by a gene gun or naked DNA administration.

The present invention likewise extends to the development and diagnostic and therapeutic uses of antibodies against the MHC I molecule, including naturally raised and recombinantly prepared antibodies. Such antibodies could include both polyclonal and monoclonal antibodies prepared by known genetic techniques, as well as bi-specific (chimeric) antibodies, and antibodies including other functionalities suiting them for additional therapeutic or diagnostic uses in connection with their capability of modulating neurite outgrowth.

The invention also relates to the identification, production and diagnostic and therapeutic uses of MHC I analogs which can be used as competitive inhibitors of soluble MHC I, thereby reducing the inhibitory effect of soluble MHC I on neurite outgrowth. While MHCI molecules are well known as membrane-bound proteins, soluble forms of MHCI (sMHC) also exist. Charlton and Zmijewski, 170 *Science* 636-7 (1970); Allison et al., 118 *Journal of Immunology* 1004-9 (1977). Soluble MHCI may be produced by the direct secretion of the full length MHC I heavy chain (with a membrane anchor) (Puppo et al., 53 *Tissue Antigens* 253-62 (1999)), alternative exon splicing (Krangel, 163 *Journal of Experimental Medicine* 1173-90 (1986)), or proteases that cleave membrane-bound MHCI (mMHCI) from its membrane anchor. Zhai and Knechtle, 59 *Human Immunology* 404-14 (1998).

The sMHCI heavy chain has been shown to be both associated with β2m (Allison et al., 1977), as well as β2 m-free. Puppo et al., 1999; Pickl et al., 151 *Journal of Immunology* 2613-22 (1993).

Thus, the MHC I analogs, and any antagonists or antibodies that may be raised thereto, are capable of use in connection with various diagnostic techniques, including immunoassays, such as a radioimmunoassay, using for example, an antibody to the MHC I that has been labeled by either radioactive addition, or radioiodination.

The invention also relates to the identification, production and diagnostic and therapeutic uses of MHC I analogs which can be used as competitive inhibitors of soluble MHC I, thereby reducing the inhibitory effect of soluble MHC I on neurite outgrowth.

Thus, the MHC I analogs, and any antagonists or antibodies that may be raised thereto, are capable of use in connection with various diagnostic techniques, including immunoassays, such as a radioimmunoassay, using for example, an antibody to the MHC I that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of the MHC I, or to identify drugs or other agents that may mimic or block its activity. The system or test kit may comprise a labeled component prepared by one of the radioactive and/or enzymatic techniques discussed herein, coupling a label to the MHC I, its agonists and/or antagonists, and one or more additional immunochemical reagents, at least one of which is a free or immobilized ligand, capable either of binding with the labeled component, its binding partner, one of the components to be determined or their binding partner(s).

It should be appreciated that also within the scope of the present invention are DNA sequences encoding MHC I analogs, wherein mutations are made in the wt MHC I DNA sequence such that one or more codons are changed to codons which code for different amino acids. Such mutations are generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino acids with nonpolar R groups
Alanine
Valine
Leucine
Isoleucine
Proline
Phenylalanine
Tryptophan
Methionine Amino acids with uncharged polar R groups
Glycine
Serine
Threonine
Cysteine
Tyrosine
Asparagine
Glutamine Amino acids with charged polar R groups (negatively charged at Ph 6.0)
Aspartic acid
Glutamic acid Basic amino acids (positively charged at pH 6.0)
Lysine
Arginine
Histidine (at pH 6.0)

Another grouping may be those amino acids with phenyl groups
Phenylalanine
Tryptophan
Tyrosine Another grouping may be according to molecular weight (i.e., size of R groups)

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
  Lys for Arg and vice versa such that a positive charge may be maintained;
  Glu for Asp and vice versa such that a negative charge may be maintained;

Ser for Thr such that a free —OH can be maintained; and Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The present invention also relates to a recombinant DNA molecule or cloned gene, or a degenerate variant thereof, which encodes an MHC I agonist or antagonist which is effective to reduce or eliminate the MHC I-induced inhibition of neurite outgrowth.

The present invention likewise contemplates pharmaceutical intervention in the cascade of reactions in which the MHC I is implicated, to modulate the inhibition of neurite outgrowth initiated by the MHC I. In a preferred embodiment, the reaction cascade involves cAMP.

As discussed earlier, the MHC I agonists or antagonists or their binding partners or other ligands or agents may be prepared in pharmaceutical compositions, with a suitable carrier and at a strength effective for administration by various means to a patient experiencing an adverse medical condition associated with specific neural disease or injury for the treatment thereof. A variety of administrative techniques may be utilized, among them parenteral techniques such as subcutaneous, intravenous and intraperitoneal injections, catheterizations and the like. Average quantities of the MHC I agonist or antagonist or their subunits may vary and in particular should be based upon the recommendations and prescription of a qualified physician or veterinarian.

Also, antibodies including both polyclonal and monoclonal antibodies, and drugs that modulate the activity of the MHC I and/or its subunits (e.g., the soluble form(s)) may possess certain diagnostic applications and may for example, be utilized for the purpose of detecting and/or measuring conditions such as viral infection or the like. For example, the MHC I or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the MHC I of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "*Hybridoma Techniques*" (1980); Hammerling et al., "*Monoclonal Antibodies And T-cell Hybridomas*" (1981); Kennett et al., "*Monoclonal Antibodies*" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against MHC I peptides can be screened for various properties; i.e., isotype, epitope, affinity, etc. Of particular interest are monoclonal antibodies that neutralize the activity of the MHC I or its subunits. Such monoclonals can be readily identified in assays. High affinity antibodies are also useful when immunoaffinity purification of native or recombinant MHC I is possible.

Preferably, the anti-MHC I antibody used in the diagnostic methods of this invention is an affinity purified polyclonal antibody. More preferably, the antibody is a monoclonal antibody (mAb). In addition, it is preferable for the anti-MHC I antibody molecules used herein be in the form of Fab, Fab', F(ab')$_2$ or F(v) portions of whole antibody molecules.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a MHC I-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present MHC I and their ability to inhibit specified MHC I activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., 8 *Virology* 396 (1959)) supplemented with 4.5 gm/l glucose, 20 mm glutamine, and 20% fetal calf serum. An exemplary inbred mouse strain is the Balb/c.

Methods for producing monoclonal anti-MHC I antibodies are also well-known in the art. See Niman et al., 80 *Proceedings of the National Academy of Sciences, U.S.A.* 4949-4953 (1983). Typically, the present MHC I or a peptide analog is used either alone or conjugated to an immunogenic carrier, as the immunogen in the before described procedure for producing anti-MHC I monoclonal antibodies. The hybridomas are screened for the ability to produce an antibody that immunoreacts with the MHC I peptide analog and the present MHC I.

The present invention further contemplates therapeutic compositions useful in practicing the therapeutic methods of this invention. A subject therapeutic composition includes, in admixture, a pharmaceutically acceptable excipient (carrier) and one or more of a MHC I agonist or antagonist, polypeptide analog thereof or fragment thereof, as described herein as an active ingredient. In a preferred embodiment, the composition comprises an antigen capable of modulating the neurite outgrowth inhibition of specific binding of the present MHC I within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of MHC I activity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration.

Alternatively, continuous intravenous infusion sufficient to maintain concentrations of ten nanomolar to ten micromolar in the blood are contemplated.

The therapeutic compositions may further include an effective amount of the MHC I antagonist or analog thereof, and one or more of the following active ingredients: an antibiotic, a steroid. As used herein, "pg" means picogram, "ng" means nanogram, "ug" or "µg" mean microgram, "mg" means milligram, "ul" or "µl" mean microliter, "ml" means milliliter, "l" means liter, "uM" means micromolar, "mM" means micrometer, "mm" means millimeter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., $E.$ $coli$ plasmids col El, pCR1, pBR322, pMB9 and their derivatives, plasmids such as RP4; phage DNAS, e.g., the numerous derivatives of phage $\lambda$, e.g., NM989, and other phage DNA, e.g., M13 and filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage $\lambda$, the control regions of fd coat protein, the promoter for 3-phosphoglycerate kinase or other glycolytic enzymes, the promoters of acid phosphatase (e.g., Pho5), the promoters of the yeast $\alpha$-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of $E.$ $coli,$ $Pseudomonas,$ $Bacillus,$ $Streptomyces,$ fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that MHC I analogs may be prepared from nucleotide sequences of the protein complex/subunit derived within the scope of the present invention. Analogs, such as fragments, may be produced, for example, by pepsin digestion of MHC I material. Other analogs, such as muteins, can be produced by standard site-directed mutagenesis of MHC I coding sequences. Analogs exhibiting "MHC I-reducing activity" such as small molecules, whether functioning as promoters or inhibitors, may be identified by known in vivo and/or in vitro assays.

As mentioned above, a DNA sequence encoding and MHC I agonist or antagonist can be prepared synthetically rather than cloned. The DNA sequence can be designed with the appropriate codons for the MHC I agonist or antagonist amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, 292 *Nature* 756 (1981); Nambair et al., 223 *Science* 1299 (1984); Jay et al., 259 *Journal of Biology and Chemistry* 6311 (1984).

Synthetic DNA sequences allow convenient construction of genes which will express MHC I analogs or "muteins". Alternatively, DNA encoding muteins can be made by site-directed mutagenesis of native MHC I genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, 244 *Science* 182-188 (April 1989). This method may be used to create analogs with unnatural amino acids.

The present invention extends to the preparation of antisense oligonucleotides and ribozymes that may be used to interfere with the expression of the MHC I at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. See Weintraub, 1990; Marcus-Sekura, 1988. In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into MHC I-producing cells. Antisense methods have been used to inhibit the expression of many genes in vitro. Marcus-Sekura, 1988; Hambor et al., 1988.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it. Cech, 1988. Because they are sequence-specific, only mRNAs with particular sequences are inactivated.

Investigators have identified two types of ribozymes, *Tetrahymena*-type and "hammerhead"-type. Hasselhoff and Gerlach, 1988. *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for MHC I and their ligands.

The present invention also relates to a variety of diagnostic applications, including methods for detecting the presence of stimuli such as the earlier referenced polypeptide ligands, by reference to their ability to reduce the neurite outgrowth inhibition which is mediated by the MHC I. As mentioned earlier, the MHC I can be used to produce antibodies to itself by a variety of known techniques, and such antibodies could then be isolated and utilized as in tests for the presence of particular MHC I activity in suspect target cells.

As described in detail above, antibody(ies) to the MHC I can be produced and isolated by standard methods including the well known hybridoma techniques. For convenience, the antibody(ies) to the MHC I will be referred to herein as $Ab_1$ and antibody(ies) raised in another species as $Ab_2$.

The presence of MHC I in cells can be ascertained by the usual immunological procedures applicable to such determinations. A number of useful procedures are known. Three such procedures which are especially useful utilize either the MHC I labeled with a detectable label, antibody $Ab_1$ labeled with a detectable label, or antibody $Ab_2$ labeled with a detectable label. The procedures may be summarized by the following equations wherein the asterisk indicates that the particle is labeled:

$$MHC\ I^*+Ab_1=MHC\ I^*Ab_1 \quad (A.)$$

$$MHC\ I+Ab^*=MHC\ I\ Ab_1^* \quad (B.)$$

$$MHCI+Ab_1+Ab_2^*=MHC\ I\ Ab_1Ab_2^* \quad (C.)$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, the MHC I forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-MHC I antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The MHC I or its binding partner(s) can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$ $^{57}Co$, $^{58}Co$, $^{59}Fe$, $^{90}Y$, 125I, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, commercial test kits suitable for use by a medical specialist may be prepared to determine the presence or absence of predetermined MHC I inhibition of neurite outgrowth on suspected target cells. In accordance with the testing techniques discussed above, one class of such kits will contain at least the labeled MHC I or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence of soluble MHC I, which may be associated with inhibition of neurite outgrowth:

(a) a predetermined amount of at least one labeled immunochemically reactive component obtained by the direct or indirect attachment a specific binding partner to MHC I to a detectable label;

(b) other reagents; and (c) directions for use of said kit.

More specifically, the diagnostic test kit may comprise:

(a) a known amount of the MHC I binding partner generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive," "sandwich, " "double antibody, " etc.), and comprises:

(a) a labeled component which has been obtained by coupling the MHC I binding partner to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the MHC I binding partner and a specific binding partner thereto.

In accordance with the above, an assay system for screening potential drugs effective to modulate the activity of the MHC I may be prepared. The MHC I in either membrane bound form or soluble form may be introduced into a test system, and the prospective drug may also be introduced into the resulting cell culture, and the culture thereafter examined to observe any changes in the neurite outgrowth activity of the cells, due to the addition of the prospective drug.

Experiments have shown that providing antibodies or compositions which contain antibodies to MHC I molecules rescues neural outgrowth, thereby modulating the effect of MHC I. Providing antibodies in this manner applies to both membrane-bound MHC I and soluble MHC I.

Experiments have also shown that providing certain pharmacological agents or compositions containing certain pharmacological agents rescues neural outgrowth, by modulating the effect of MHC I molecules. Such pharmacological agents comprise agents that reduce the expression of MHC I; agents that block MHC I molecules from interacting with their receptor; agents that interfere with the MHC I receptor binding site; and agents that interfere with the signaling pathway of the MHC I receptor. The effect of these agents applies to both membrane-bound and soluble MHC I.

As is evident from the previous discussion, the present invention allows one to modulate neuronal outgrowth by using the properties of MHC I molecules. Appropriate pharmacological agents may be administered which either enforce or minimize the effects of MHC I, thereby producing the desired result. This flexibility in modulating neuronal outgrowth is previously unknown, and serves as a great advance in the treatment of neuronal disease, injury, and abnormality.

Compositions for Modulating Neuronal Outgrowth

The compositions of the present invention may be administered for therapy by any suitable route, including topical (including opthalmic and to mucous membranes including vaginal and rectal delivery), pulmonary (including by inhalation or insufflation of powders or aerosols, including by nebulizer), intratracheal, intranasal, oral, and parenteral (including intraperitoneal, subcutaneous, intramuscular, intravenous, intradermal, intracranial, intra-spinal cord, and transdermal) routes. It will be appreciated that the preferred route will vary with the condition and age of the patient, the nature of the disorder and the chosen active ingredient including other therapeutic agents. Preferred is the parenteral route. However, other routes may also be utilized depending on the conditions of the patient and how long-lasting the treatment is.

Compositions for topical administration may include transdermal patches, ointments, lotions, creams, gels, drops, suppositories, sprays, liquids and powders.

Compositions for oral administration include powders, granules, suspensions, solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives such as, but not limited to, penetration enhancers, carrier compounds and other pharmaceutically acceptable carriers and excipients.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The compositions of the present invention are prepared in accordance with accepted pharmaceutical procedures. For example, the procedures as described in *Remington's Pharmaceutical Sciences*, seventeenth edition, editor Alfonso R. Gennaro, Mack Publishing Company, Easton, Pa. (1985).

The dosage of the pharmaceutical composition of matter for modulating neuronal outgrowth in a mammal, pharmaceutically acceptable salts thereof, or mixtures thereof, in the compositions of the invention administered to a patient will vary depending on several factors, including, but not limited to, the age, weight, and species of the patient, the general health of the patient, the severity of the symptoms, whether the composition is being administered alone or in combination with other agents, the incidence of side effects and the like.

Many dosage forms for the present invention are possible, and include tablets, capsules, liquid syrups, soft gels, suppositories, and enemas. The composition may be formulated as a suspension in aqueous, non-aqueous, or mixed media. Aqueous suspensions may further contain substances which increase the viscosity of the suspension, including, but not limited to, sodium carboxymethylcellulose, sorbitol, and/or dextran. The suspension may also contain stabilizers.

In general, a dose suitable for application in the treatment of neuronal damage is about 0.1-100 mg/kg body weight/dose per day. The desired dose may be administered as 1 or more subdoses administered at appropriate intervals throughout the day. The compounds may be administered repeatedly over a period of months or years, or it may be slowly and constantly infused to the patient. Higher and lower doses may also be administered.

To achieve good plasma concentrations, the active compounds may be administered, for instance, by intravenous injection of a solution of the active ingredient, optionally in saline, or orally administered as a bolus.

In order to further illustrate the present invention and the advantages thereof, the following specific examples are given, it being understood that same are intended only as illustrative and as nowise limitative.

EXAMPLES

The effects of neuronal MHC I expression on neuronal outgrowth and repair responses were studied. Using an organotypic culture system, neurons expressing MHC I inhibited retinal neurite outgrowth at long distance. This neuro-inhibition was mediated by a secreted form of MHC I and could be antagonized by MHC I antibodies or a cAMP antagonist. In vivo, the expression of MHC I on the neurons of transgenic mice diminished/inhibited/attenuated neuronal repair responses following CNS injury. As many CNS pathological conditions lead to local increases in MHC I, treatments that limit the neuro-inhibitory effects of MHC I provide novel treatments for CNS disorders.

Example 1

To evaluate the role of MHC I in neuronal development, a series of experiments was performed using an organotypic co-culture system in which embryonic retinal tissue is cultured a short distance from its thalamic target in a nutritive gel matrix. Normally, over a period of a few days, the retinal tissue extends neurite projections to the thalamus. A retinal explant was juxtaposed from a wild-type (wt) C57BL/6 (H2-$D^b$) mouse with thalamic tissue from either a wt mouse, or from a C57B16 transgenic mouse whose neurons were engineered to express MHCI $D^b$ (referred herein as MHC I-tg mice). Rall et al. (1995) 182(5) *Journal of Experimental Medicine* 1201 (1995).

The MHC-tg mice possesses a transgene consisting of a MHC I $D^b$ gene linked to a neuron-specific enolase promoter. Rall, 1995. E14 day embryos from C57BL/6 mice which were homozygous for the MHC I $D^b$ transgene, or from wt (C57BL/6) mice, were placed into petri dishes containing Leibovitz's L-15 media (Gibco BRL) and the retinas and thalami were isolated. A wt retina was then placed (0.5 mm from a wt, or a MHC-tg, thalamus in a matrigel matrix (Growth Factor Reduced Basement membrane matrix, Collaborative Biomedical Products) in an 8 chamber slide (Fischer LabTech) on ice. The slides were then incubated at 37° C. for 30-60 minutes to solidify the gel. Neurobasal medium (Gibco BRL, containing L-glutamine, antibiotics and 1× B27 supplement) was added to each chamber (0.2 ml). The co-cultures were coded and incubated further (at 37° C., 5% $CO_2$) for 4-5 days. The experiment was then terminated by replacing the media with 4% PFA and storing the slides at 4° C. The co-cultures were scored in a subjective manner by 2 blinded individuals for the relative extent of retinal neurite outgrowth towards the thalamus (on a scale of 0-100). Cultures were scored for the overall length of retinal neurite outgrowth toward the thalamus. Significant changes in the number of neurites were not observed, nor were significant turning of axon direction. After scoring, the control wt retina-wt thalamus co-culture scores were adjusted to represent 100% outgrowth, and all other co-culture scores were adjusted by the same factor. The scores are expressed as the mean relative outgrowth±standard error of the mean (SEM) relative to the control cultures. Duplicates of each group were tested simultaneously in 4 separate experiments.

Wild type retinas that were cultured near to a wt thalamus grew extensive projections toward the thalamus (FIGS. 1A, 1C). However, wt retinas co-cultured with MHC I-tg thalami displayed limited outgrowth, especially on the side facing the thalamic explant (FIGS. 1B, 1C) ($p<0.001$). This long-distance inhibition of neurite outgrowth suggested that the MHC 1-tg thalami secreted a neuro-inhibitory factor(s), or were deficient in secreting a chemo-attractant(s).

Example 2

While MHC I is well known as a membrane bound molecule, secreted forms of MHC I (sMHC I) are also naturally produced and have been shown to inhibit T cell responses. Charlton and Zmijewski, 170(958) *Science* 636 (1970); Allison et al., 118(3) *Journal of Immunology* 1004 (1977); Gussow and Ploegh, 8 *Immunology Today* 220 (1987); Buelow et al., 59(5) *Transplantation* 649 (1995); Krangel, 163(5) *Journal of Experimental Medicine* 1173 (1986); Zhai et al., 59(7) *Human Immunology* 404 (1998); Puppo et al., 53(3) *Tissue Antigens* 253 (1999).

The following experiments address whether the long-distance inhibition of neurite outgrowth by MHC-tg thalami was mediated by sMHC I. All antibodies were coded and added to co-cultures of wt retinas with MHC-tg thalami in a blinded fashion. Anti-MHC I $D^b$ (Pharmingen), anti-MHC I $D^k$ (Pharmingen), anti-GAD (Chemicon) monoclonal antibody, or mouse IgG2a (Sigma) (all at 0.002 mg/ml) were added to the matrigel (prior to its solidification) and to the media. Both the anti-$D^b$ and anti-$D^k$ monoclonal antibodies are of the IgG2a isotype. In addition to these experimental groups, each experiment contained positive control co-cultures of wt retinas confronted with wt thalami. The co-cultures were incubated, fixed and scored in a blinded fashion, as described above. Duplicates of each group were tested simultaneously in 4 separate experiments.

Addition of a MHCI $D^b$-specific monoclonal antibody to the explant co-cultures rescued the ability of retinal tissue to extend processes towards a MHC-tg thalamus ($p<0.005$) (FIG. 1C). In contrast, addition of isotype matched monoclonal antibodies against MHCI $D^k$, glutamic acid decarboxylase (GAD, another neuronal antigen), or mouse IgG2a, failed to rescue neurite outgrowth from retinas that were co-cultured with a MHC I-tg thalamus (FIG. 1C).

Example 3

Next, the neuro-inhibitory activity of conditioned media from wt and MHC I-tg thalamic cultures was examined.

Wt or MHC-tg thalami from 8-12 E14 fetuses were cultured for 3-5 days in Neurobasal media with L-glutamine, antibiotics and 1× B27 supplement. The conditioned media was harvested and added to fresh wt retina-wt thalamus explant co-cultures at dilutions of 1:1, 1:4, 1:20 and 1:100. Both the conditioned media and the antibodies were coded. The co-cultures were incubated 4-5 days and scored in a blinded fashion as described above. Data shown is for cultures containing 1:1 dilution of conditioned media with fresh media. Duplicates of each group were tested simultaneously in 4 separate experiments.

Conditioned media from wt thalamic explant cultures had no effect on retinal neurite extension (FIG. 1D), while conditioned media from MHCI-tg thalamic explant cultures greatly inhibited retinal neurite outgrowth (FIG. 1C). Again, addition of anti-MHCI $D^b$, but not anti-MHCI $D^k$, to the conditioned media from MHC-tg thalamic cultures significantly reduced its inhibitory activity ($p<0.005$) (FIG. 1D).

Example 4

Figure 2:
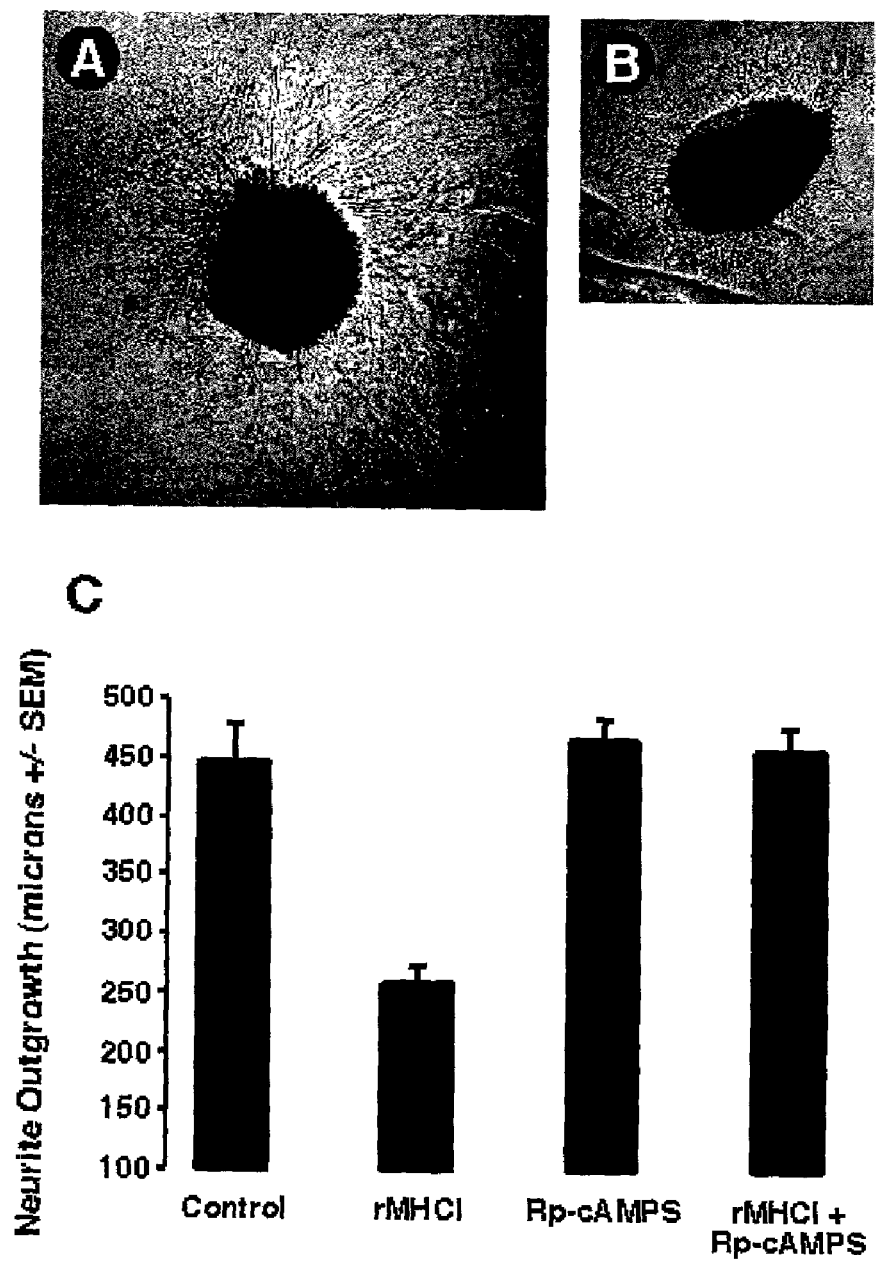
FIG. 2 shows inhibition of retinal axonal outgrowth by rMHC I.

To rule out the possibility that the MHC I-tg thalami inhibit retinal growth indirectly due to an alteration in the milieu of neuroactive molecules they secrete, wt retinas were cultured alone, in the presence, or absence of recombinantly produced MHC I $D^b$ (rMHC I). The rMHC I was obtained by transfecting COS cells with a recombinant plasmid that directs the expression of a MHC I $D^b$ lacking a membrane anchor and harvesting the conditioned media. Retinas that were cultured with rMHC I extended significantly shorter neurites than did controls (FIGS. 2A, 2B).

A truncated MHC I $^{Db}$ mini-gene (containing exons 1-4 plus a stop codon) was subcloned into pIRES (Invitrogen). Due to the lack of a transmembrane spanning region (exons 5 and 6), this MHC I molecule is secreted. COS cells were transfected (using lipofectamine, GIBCO) with the parental plasmid, or the plasmid encoding soluble MHC I $D^b$. The COS cell transfection efficiencies with the parental plasmid and the soluble MHC I encoding plasmid were similar, as judged by the FACs analysis of GFP expression (which is encoded by the pIRES plasmid). Forty eight hours later, the conditioned media was harvested and added to fresh explant co-cultures of wt retina and thalamus at final dilutions of 1:1, 1:4, 1:20 or 1:100. To some cultures, monoclonal antibodies to MHCI $D^b$ or $D^k$ were added to both the matrigel (before its solidification) and the media (0.005 mg/ml). Both the conditioned media and the antibodies were coded. The co-cultures were incubated for 4-5 days, fixed, and scored in a blinded fashion as described above. Duplicates of each group were tested simultaneously in 4 separate experiments. Data shown is for cultures containing a 1:1 dilution of conditioned media with fresh media.

Example 5

Cyclic nucleotide-dependent signaling pathways are shared by several neuronal guidance cues including the neurotrophins, netrins, and semaphorins. Depending on the levels of cyclic nucleotide in the neuron, the response of the growth cone to these guidance cues can be either attractive of repulsive. Although these guidance molecules all have different receptors and possibly trigger different initial signals, the downstream mechanisms are likely to involve phospolipase C, phosphoinositol-3 kinase, or $Ca^{2+}$ pathways that modulate cyclic nucleotide levels.

To test whether a soluble form of MHC I is acting through a similar mechanism to inhibit neurite outgrowth, a retina (alone) explant culture system (with and without recombinant MHC I, rsMHC I) was used to measure axonal outgrowth in the presence of various compounds that influence cyclic nucleotide-dependent pathways.

E14 day embryos from C57Bl6 and Balb/c mice were dissected in Leibovitz's L-15 media (Gibco BRL). The retinas were isolated and placed in a matrigel matrix (Growth Factor Reduced Basement membrane matrix, Collaborative Biomedical Products) in a chamber slide (Fisher LabTech). The slides were then incubated at 37° C. for 60 minutes to solidify the gel. Neurobasal medium (Gibco BRL), containing L-glutamine, antibiotics and 1× B27 supplement) was added to each chamber (0.25 ml). Inhibition of axon outgrowth by rsMHC I was tested by addition of conditioned culture media from COS cells containing rsMHC I or control media to the normal culture media. Compounds that modulate cAMP levels were added at the following concentrations to the matrigel and the culture media: Forskolin (5 uM), a drug that activates adenyl cyclase and endogenous production of cAMP; and Rp-cAMPS (20 uM), the R diasteriomer of adenosine 3',5'-(cyclic) phosphorothioate, a non-hydrolyzable antagonist of cAMP. The cultures were incubated further at 37° C., 5% $CO_2$. After incubating for 3 days, the experiment was terminated by replacing the buffer with 4% PFA and storing the slides at 4° C. Statistical Analysis was done by Student's test.

When C57Bl6 E14 retinas were cultured in the presence of rsMHC I, there was significantly less neurite extension compared to controls without rsMHC I ($p=0.00001$). Addition of Rp-cAMPS had no effect on retinal explant outgrowth in control cultures (media alone). However, when Rp-cAMPS (20 uM) was included in cultures containing rsMHC I, it completely prevented the inhibitory effects of rsMHC I (difference from control media alone p=0.69) (FIG. 2C).

Figure 5:
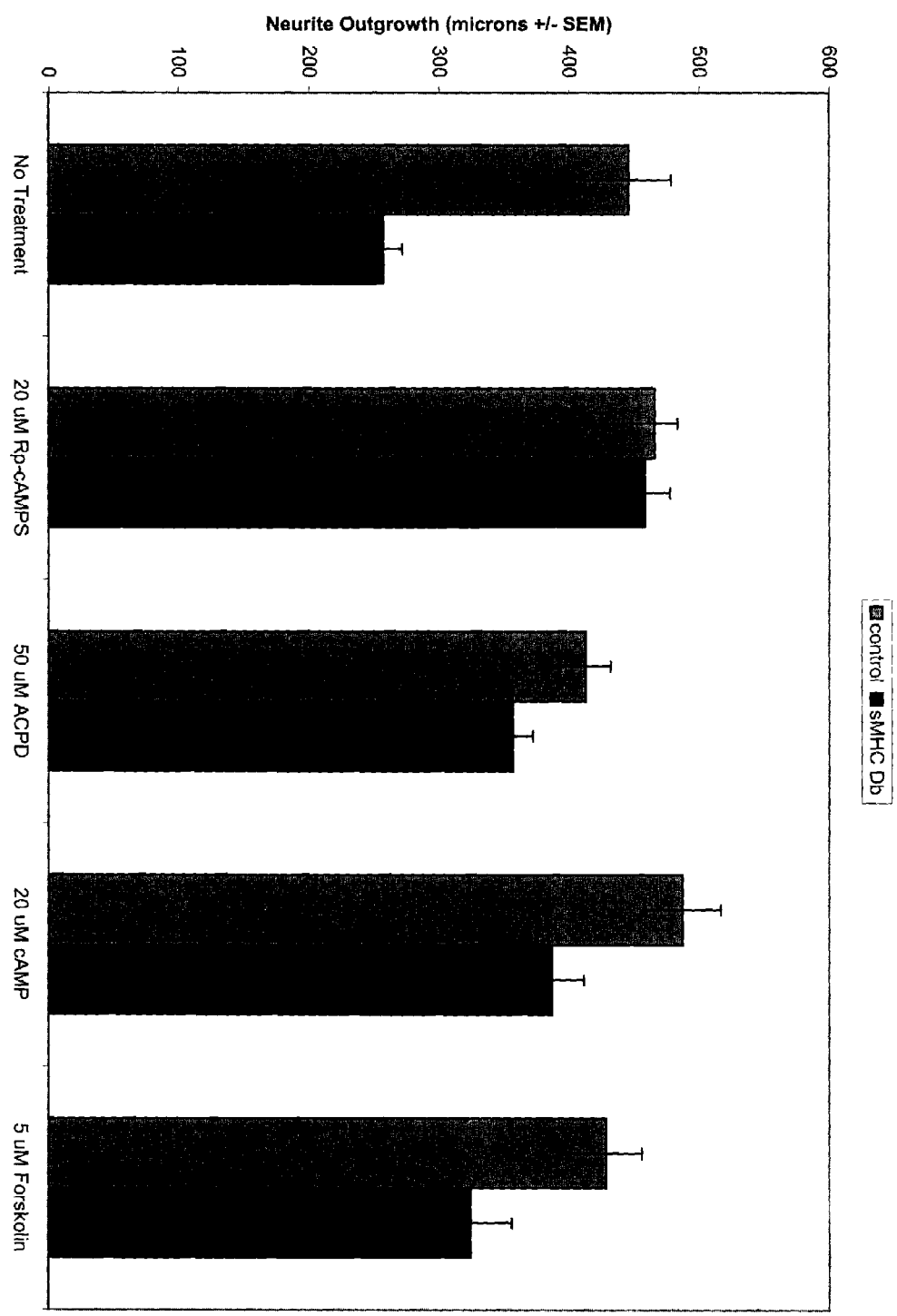
FIG. 5 evidences the effects of certain drugs on cyclic nucleotide-dependent signaling pathways by showing axonal outgrowth in a retina explant culture system (with and without recombinant MHC I, rsMHC I) in the presence of various compounds, including Rp-cAMPS, ACPD, cAMP, and Forskolin.

Further experiments were done adding ACPD (1-amino-(1S,3R)-cyclo pentanedicarboxylic acid, 50 uM), cAMP (20 uM) or Forskolin (5 uM). ACPD is a specific metabotropic glutamate receptor agonist that reduces the neuronal cAMP and therefore should have a similar effect as an antagonist of cAMP. cAMP and Forskolin should act to raise cAMP levels. Forskolin activates the enzyme (adenylate cyclase) that makes cAMP, thus increasing levels of cAMP. The addition of ACPD significantly enhanced neurite outgrowth compared to cultures with rsMHC I alone (P=0.001). However, this enhancement did not return to control levels (P=0.004). The addition of cAMP also significantly enhanced neurite outgrowth compared to cultures with rsMHC I alone (P=0.0001), and returned the outgrowth to levels that were not statistically different from control levels (p=0.08). Finally, the addition of forskolin tended to enhance neurite outgrowth compared to cultures with rMHC I alone (P=0.0496), but this slight enhancement did not return the outgrowth to control levels (P=0.0005). These data show that Rp-cAMPS is very efficient at blocking the effects of rsMHC I, while ACPD and cAMP are partially protective and Forskolin shows a non-significant trend towards protection (FIG. 5).

cAMP thus appears to act as a downstream signal from MHC I/receptor interaction. Decreasing cAMP levels (with Rp-cAMPS) can reverse this inhibitory effect by blocking the signaling cascade. ACPD also partially neutralize the effects of rsMHC I. Increasing cAMP levels with cAMP itself, or drugs which increase cAMP levels (e.g., Forskolin) can also partially neutralize the inhibitory action of rMHC I. As the cyclic nucleotide pathways interact with many other messenger systems in a complex manner, it is not surprising that both cAMP antagonists and agonists can inhibit the neuroinhibitory actions of rMHC I. These results suggest that at least part of the mechanism behind the inhibitory action of MHC I involves a cyclic nucleotide dependent pathway. MHC I may be a bifunctional guidance cue, exerting either negative or positive influences on axon growth depending on levels of cyclic nucleotide or other components of a cyclic nucleotide-dependent pathway.

While addition of the cAMP antagonist Rp-cAMPs had no effect on retinal explant outgrowth, its inclusion in cultures containing rMHC I completely prevented the inhibitory effects of rMHC I (FIG. 2C), suggesting that part of the mechanism behind the inhibitory action of MHC I involves a cyclic nucleotide pathway.

Retinas also extended fewer and shorter neurites toward COS cells transfected with plasmids that expressed the full length MHCI $D^b$ (possessing a membrane anchor). Retinas displayed normal outgrowth toward control COS cells (70% average outgrowth after 3 days in culture), while they only displayed 40% outgrowth toward COS cells expressing full length MHCI $D^b$, and made fewer contacts with these COS cells.

Example 6

In animal models, IFNγ, TNFα, kainate-induced seizures and axotomy of motor neurons have been shown to induce neuronal MHC I expression. Neumann et al., 1995; Neumann et al., 1997, Corriveau et al., 1998; Linda et al., 150(2) *Experimental Neurology* 282 (1998); Linda et al., 101(1) *Journal of Neuroimmunology* 76 (1999); Wong et al., 310(5979) *Nature* 688 (1984); Drew et al., 150(8, Part 1) *Journal of Immunology* 3300 (1983). Numerous studies have observed increases in MHC I expression in the CNS of patients with brain injury, stroke, epilepsy and neurodegenerative diseases. Neumann et al., 1997; Linda et al., 1999, Wong et al., 1984; O'Malley and MacLeish, 43(1-2) *Journal of Neuroimmunology* 45 (1993); Feuerstein et al., 5(3-4) *Neuroimmunomodulation* 143 (1998).

Based on the MHC I-mediated inhibition of neuronal sprouting responses observed in vitro, the following experiments were performed to determine whether the neuronal expression of MHC I in neuropathological conditions might counteract neuronal repair mechanisms. A well-characterized neuronal repair model that involves the unilateral lesioning of the perforant path to the hippocampus was utilized. Lynch et al., 42(2) *Brain Research* 311 (1972); Cotman et al., 70(12) *Proceedings of the National Academy of Sciences, U.S.A.* 3473 (1973); Lynch et al., 180(93) *Science* 1364 (1973); Steward, 194(4263) *Science* 426 (1976); Scheff et al., 199(1) *Brain Research* 21 (1980); Stanf and Cowan, 232(1) *Brain Research* 162 (1982); Frotscher et al., 20(5) *Trends in Neuroscience* 218 (1997); Ramirez, 73 *Advanced Neurology* 61 (1997). In response to the denervation, septal hippocampal cholinergic neurons sprout into the outer molecular layer (ML) of the hippocampus. Concurrent with this sprouting into the ML, there is a recovery in the animal's performance of hippocampal-dependent spatial tasks. Douglas and Raphelson, 62(2) *Journal of Comparative Physiology and Psychology* 320 (1966); Scheff and Cotman, 21(2) *Behavioral Biology* 286 (1977). Before lesioning, sections from wt (C57Bl6) and C57Bl6 MHC I-tg mouse brains had no discernable differences in their cholinergic staining patterns (e.g., see unlesioned sides in FIGS. 3A and 3B), or in their ability to perform a hippocampal-dependent spatial task. Scheff and Cotman, 1977.

Eight-12 weeks old C57Bl/6 mice which were homozygous for the MHCI $D^b$ transgene, or control wild type C57BL/6 mice were anesthetized and placed into a stereotaxic device. A trench was drilled into the skull 1 mm lateral of lambda, and was extended 3 mm toward the temporal ridge. Using a micro-dissecting knife mounted on the stereotaxic device, the lesion was made 3 mm deep and 2.5 mm medial to lateral. The wound was closed and treated with antibiotic. After 14 days, the mice were perfused with 4% PFA, the brains were frozen, and slices stained for AChE as previously described. Cotman et al., 1973, Lynch et al., 1973, Lanier, 16 *Annual Review of Immunology* 359 (1998).

Figure 3:
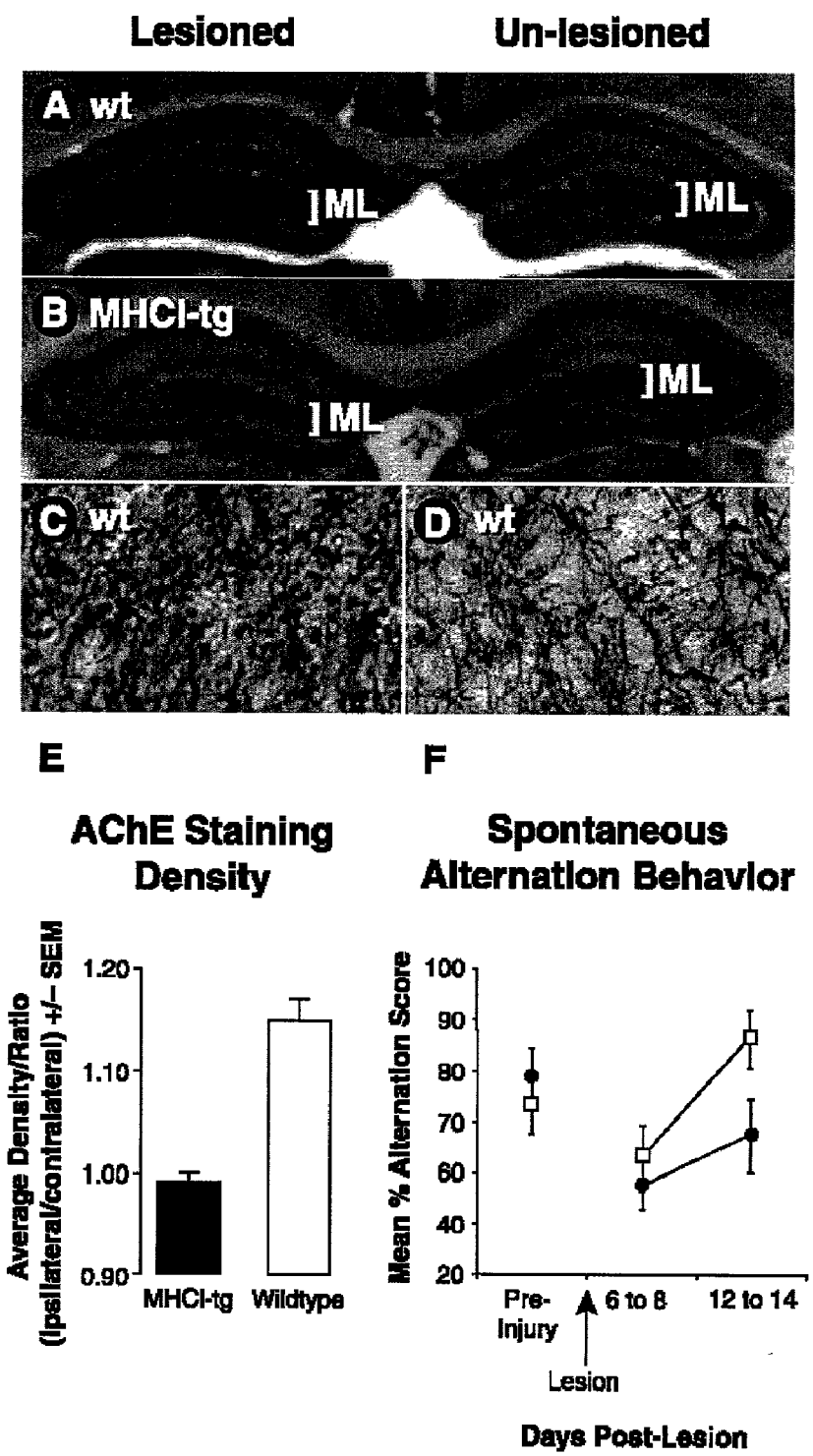
FIG. 3 shows neuronal expression of MHC I inhibits compensatory sprouting responses in the hippocampus after perforant path lesioning. The perforant path of 8-12 weeks old male wt C57Bl6 or MHC I-tg mice was unilaterally lesioned using a stereotactic device, essentially as described in Cotman et al., 70(12) *Proceedings of the National Academy of Sciences, U.S.A.* 3473 (1973); Lynch et al., 180(93) *Science* 1364 (1973); Steward et al., 18(4) *Experimental Brain Research* 396 (1973). After 14 days, the mice were perfused and coronal brain sections were stained for AChE. Hedreen et al., 33(2) *Journal of Histochemistry and Cytochemistry* 134 (1985).
Figure 4:
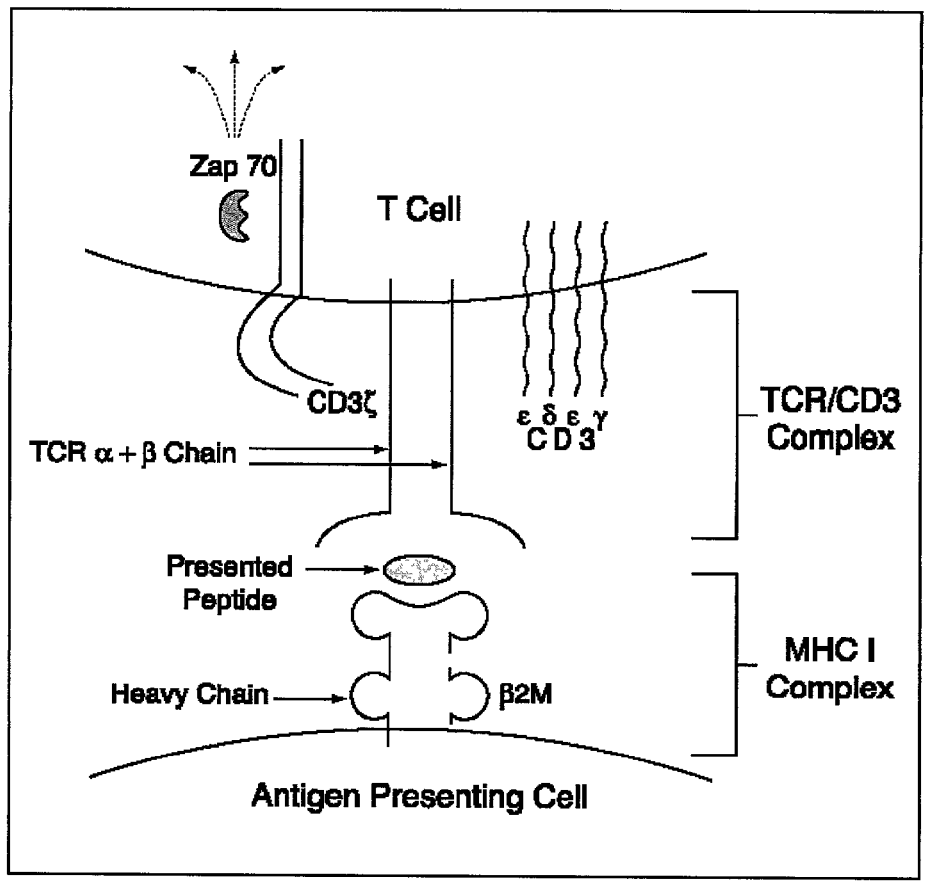
FIG. 4 is a schematic of the interaction between TcR and MHC I.

Following unilateral perforant path lesioning, the density of cholinergic fiber staining on the lesioned side was compared to the non-lesioned side on the same hippocampal microsection (thereby circumventing possible staining artifacts). By 14 days post lesion, a robust compensatory sprouting response was seen on the lesioned side of wt mice (FIGS. 3 A-E), and the mice recovered their ability to perform a hippocampal-dependent spatial task (FIG. 3F). In MHC I-tg mice however, the density of AChE staining in the molecular layer on the lesioned side did not increase (FIGS. 3B, 3E) ($p \leq 0.05$) and the mice did not recover to their pre-lesion task performance ability during the observation period (FIG. 3F). Thus, both histological and behavioral testing provide evidence of significantly reduced neuronal repair responses following CNS injury in MHC I-tg mice.

Both in vitro and in vivo studies indicate that the ectopic expression of MHC I can be a potent inhibitor of neuronal sprouting responses. The neuro-inhibitory activity of MHC I that we have observed may be a neurological counterpart of its inhibitory action on T cells or NK cells that engage MHC in the absence of co-stimulatory signals. Charlton and Zmijewski, 1970; Allison et al., 1977, Gussow and Ploegh, 1987; Buelow et al., 1995; Krangel, 1986; Zhai and Knechtle, 1998, Puppo et al., 1999, Lanier, 1998. Thus, up-regulation of neuronal MHC I expression in neuropathological conditions, as well as the local infiltration of MHC I expressing immune cells to damaged areas, may counteract neurorepair mechanisms in the mature CNS. In this case, treatments that limit the neuro-inhibitory actions of MHC I may promote neuronal outgrowth and provide novel treatments for brain injury and CNS disorders.

All documents referenced herein should be considered as incorporated by reference herein in their entireties for all purposes.

What is claimed is:

1. A method for enhancing neurite outgrowth, comprising contacting neurons which express a major histocompatibility complex Class I (MHC I) molecule with an effective amount of an antibody which binds to the MHC I molecule and inhibits the binding of the MHC I molecule to its receptor.

2. The method of claim 1, wherein the neurons are in an animal.

3. The method of claim 1, wherein the neurons are in culture.

4. The method of claim 1, wherein the neurons are CNS neurons.

5. The method of claim 1, wherein the neurons express membrane-bound MHC I.

6. The method of claim 1, wherein the neurons express soluble MHC I.

7. The method of claim 1, wherein the antibody is an MHC I Db-specific monoclonal antibody.

* * * * *